US008227449B2

(12) United States Patent
Oreste et al.

(10) Patent No.: US 8,227,449 B2
(45) Date of Patent: Jul. 24, 2012

(54) GLYCOSAMINOGLYCANS DERIVED FROM K5 POLYSACCHARIDE HAVING HIGH ANTICOAGULANT AND ANTITHROMBOTIC ACTIVITIES AND PROCESS FOR THEIR PREPARATION

(75) Inventors: Pasqua A. Oreste, Milan (IT); Giorgio Zoppetti, Milan (IT)

(73) Assignee: Glycores 2000 S.R.L., Milan (IT)

( * ) Notice: Subject to any disclaimer, the term of this patent is extended or adjusted under 35 U.S.C. 154(b) by 0 days.

(21) Appl. No.: 13/186,359

(22) Filed: Jul. 19, 2011

(65) Prior Publication Data
US 2011/0281820 A1 Nov. 17, 2011

Related U.S. Application Data

(63) Continuation-in-part of application No. 12/198,426, filed on Aug. 26, 2008, which is a continuation of application No. 09/950,003, filed on Sep. 12, 2001, now abandoned, which is a continuation-in-part of application No. 09/738,879, filed on Dec. 18, 2000, now abandoned.

(30) Foreign Application Priority Data

Mar. 30, 2000 (IT) .............................. MI2000A0665

(51) Int. Cl.
*A61K 31/727* (2006.01)
*C08B 37/10* (2006.01)
*C12P 19/04* (2006.01)

(52) U.S. Cl. ....... 514/54; 536/1.11; 536/123.1; 435/101
(58) Field of Classification Search ................. 536/1.11, 536/123.1; 514/54; 435/101
See application file for complete search history.

(56) References Cited

U.S. PATENT DOCUMENTS

| | | | |
|---|---|---|---|
| 4,727,063 A | | 2/1988 | Naggi et al. |
| 5,262,403 A | * | 11/1993 | Nicolson et al. ................. 514/56 |
| 5,550,116 A | * | 8/1996 | Lormeau et al. ................. 514/56 |
| 5,599,801 A | * | 2/1997 | Branellec et al. ............... 514/56 |
| 5,728,554 A | | 3/1998 | Bayer et al. |
| 5,795,875 A | | 8/1998 | Holme et al. |
| 5,958,899 A | | 9/1999 | Zoppetti et al. |
| 6,162,797 A | * | 12/2000 | Zoppetti et al. ................. 514/54 |
| 6,197,943 B1 | * | 3/2001 | Casu et al. ....................... 536/21 |
| 6,329,351 B1 | | 12/2001 | Naggi et al. |
| 2002/0062019 A1 | | 5/2002 | Oreste et al. |
| 2003/0023079 A1 | | 1/2003 | Oreste et al. |
| 2005/0027117 A1 | | 2/2005 | Oreste et al. |
| 2005/0215518 A1 | | 9/2005 | Oreste et al. |
| 2009/0105192 A1 | | 4/2009 | Oreste et al. |

FOREIGN PATENT DOCUMENTS

| | | |
|---|---|---|
| WO | 96/14425 | 5/1996 |
| WO | 97/43317 | 11/1997 |
| WO | 98/42754 | 10/1998 |
| WO | WO 9842754 * | 10/1998 |
| WO | 01/72848 | 10/2001 |
| WO | 02/50125 | 6/2002 |

OTHER PUBLICATIONS

Malmstrom et al, The J. Biol. Chem. 1980, 255(9), 3878-3883.*
Bjornsson et al. "Effects of N-deacetylation and N-desulfation of heparin on its anticoagulant activity and in vivo disposition" J. Pharmacol. Exp. Ther. 245:804-808 (1988).
Malmstrom et al. "Biosynthesis of heparin. Partial purification of the uronosyl C-5 epimerase" J. Biol. Chem. 255:3878-3883 (1980).
Nagasawa et al. "Chemical sulfation of preparations of chondroitin 4- and 6-sulfate, and dermatan sulfate. Preparation of chondroitin sulfate E-like materials from chondroitin 4-sulfate" Carbohydrate Res. 158:183-190 (1986).
Naggi et al. "Generation of anti-factor Xa active, 3-O-sulfated glucosamine-rich sequences by controlled desulfation of oversulfated heparins" Carboyhydrate Res. 336:283-290 (2001).
Naggi et al. "Toward a biotechnological heparin through combined chemical and enzymatic modification of the *Escherichia coli* K5 polysaccharide" Seminars in Thrombosis and Hemostasis 27:437-443 (2001).
Rusnati et al. "Biotechnological Engineering of heparin/heparin sulphate: A novel area of multi-target drug discovery" Curr. Pharma. Design 11:2489-2499 (2005).
Uchiyama et al. "Changes in the structure and biological property of N-O sulfate-transferred, N-resulfated heparin" J. Biol. Chem. 266:6756-6760 (1991).
International Search Report for PCT/IB01/02492, two pages, mailed Jun. 26, 2002.
International Preliminary Examination Report for PCT/IB01/02492, two pages, mailed Oct. 7, 2002.
Barrowcliffe et al. "Clinical studies in prophylaxis of thrombosis" in *Low Molecular Weight Heparin*, Wiley, pp. 153-181 (1992).
Lassen et al. "Efficacy and safety of prolonged thromboprophylaxis with a low molecular weight heparin (dalteparin) after total hip arthroplasty—the Danish prolonged prophylaxis (DPP) study" Thrombosis Res. 89:281-287 (1998).
Motsch et al. "Update in the prevention and treatment of deep vein thrombosis and pulmonary embolism" Curr. Opin. Anaesthesiology 19:52-58 (2006).
Oreste & Zoppetti "Semi-synthetic heparinoids" in *Handbook of Experimental Pharmacology*, vol. 207, Lever et al. (eds.), Springer, three pages (2012).

* cited by examiner

*Primary Examiner* — Shaojia Anna Jiang
*Assistant Examiner* — Ganapathy Krishnan
(74) *Attorney, Agent, or Firm* — Nixon & Vanderhye P.C.

(57) ABSTRACT

Glycosaminoglycans derived from K5 polysaccharide having high anticoagulant and antithrombotic activity and useful for the control of coagulation and as antithrombotic agents are obtained starting from an optionally purified K5 polysaccharide by a process comprising the steps of N-deacetylation/N-sulfation, C5 epimerization, O-oversulfation, selective O-desulfation, 6-O-sulfation, N-sulfation, and optional depolymerization, in which said epimerization is performed with the use of the enzyme glucoronosyl C5 epimerase in solution or in immobilized form in the presence of divalent cations. New, particularly interesting antithrombin compounds are obtained by controlling the reaction time in the selective O-desulfation step and submitting the product obtained at the end of the final N-sulfation step to depolymerization.

38 Claims, 17 Drawing Sheets

GLYCOSAMINOGLYCANS DERIVED FROM K5 POLYSACCHARIDE HAVING HIGH ANTICOAGULANT AND ANTITHROMBOTIC ACTIVITIES AND PROCESS FOR THEIR PREPARATION

CROSS REFERENCE TO RELATED APPLICATIONS

This application is a continuation-in-part of application Ser. No. 12/198,426, filed Aug. 26, 2008; which is a continuation of application Ser. No. 09/950,003, filed Sep. 12, 2001, abandoned; which is a continuation-in-part of application Ser. No. 09/738,879 filed Dec. 18, 2000, abandoned; which claims priority benefit of Italian application Serial No. MI2000A000665, filed Mar. 30, 2000.

FIELD AND OBJECT OF THE INVENTION

The present invention concerns new glycosaminoglycans derived from K5 polysaccharide which show all the biological characteristics of heparin of extractive origin, at a substantially similar or even higher extent.

In particular, the invention concerns new N-deacetylate N-sulfate derivatives of K5 polysaccharide, epimerized at least till 40% of iduronic acid with respect to the total uronic acids, having molecular weight from 2,000 to 30,000 D, containing from 25 to 50% by weight of the chains with high affinity for ATIII and having an anticoagulant and antithrombotic activity expressed as ratio HCII/Anti-Xa comprised between 1.5 and 4, said new derivatives of K5 polysaccharide being also active on all the coagulation parameters, as heparin is, in particular on the Anti-IIa (antithrombin) and aPTT (global anticoagulant activity), with a Anti-Xa/aPTT ratio lower than that of heparin, hence with a lesser risk of bleeding when administered to treat coagulation disorders, in particular thrombosis.

The present invention also concerns a process for the preparation of said N-deacetylate N-sulfate derivatives of K5 polysaccharide, comprising in sequence the preparation of K5 polysaccharide from *Escherichia coli*, N-deacetylation and N-sulfation, C5 epimerization of D-glucuronic acid to L-iduronic acid, oversulfation, selective O-desulfation, selective 6-0 sulfation and N-sulfation, wherein said C5 epimerization is performed using the enzyme glucuronosyl C5 epimerase in solution or in immobilized form in presence of divalent cations. More generally, the invention provides a method for improving the C5-epimerization of the glucuronyl unit of an N-deacetylated N-sulfated K5 polysaccharide by carrying out said epimerization in the presence of at least one bivalent cation selected from the group consisting of barium, calcium, magnesium and manganese ions.

The present invention further concerns a process for the preparation of novel K5 glycosaminoglycans according to the above reactions' sequence, wherein each step is carried out under precise conditions and wherein the selective O-desulfation step is carried out by treating an organic base salt of the O-oversulfated product obtained in the precedent step, with a mixture dimethyl sulfoxide/methanol at 50-70° C. for 135-165 minutes; whichever product obtained at the end of one of the steps from the C5 epimerization step onward may be submitted a depolymerization; and the novel products thus obtained.

The present invention further concerns pharmaceutical compositions comprising the new K5 glycosaminoglycans as active ingredients.

BACKGROUND OF THE INVENTION

Glycosaminoglycans, such as heparin, heparan sulfate, dermatan sulfate, chondroitin sulfate and hyaluronic acid, are biopolymers industrially extracted from different animal organs.

In particular heparin, principally obtained by extraction from intestinal pig mucosa or bovine lung, is a mixture of chains consisting of repeating disaccharide units formed by an uronic acid (L-iduronic acid or D-glucuronic acid) and by an amino sugar (glucosamine), joined by $\alpha$-1→4 or $\beta$-1→4 bonds. The uronic acid unit may be sulfated in position 2 and the glucosamine unit is N-acetylated or N-sulfated and 6-O sulfated. Moreover, glucosamine contains a sulfate group in position 3 in an amount of about 0.5%. Heparin is a polydisperse copolymer with a molecular weight ranging from about 3,000 to about 30,000 D. In particular, extractive heparin contains about 70% iduronic units and about 30% glucuronic units (Casu B., Adv. Carb. Chem. Biochem., 1985, 43, 51-134).

Besides the main anticoagulant and antithrombotic activities, heparin also exerts antilipemic, antiproliferative, antiviral, anticancer and antimetastatic activities. To satisfy the major request of starting material for these new therapeutic areas a new alternative route of production different from the extractive ones from animal tissues is necessary.

The natural biosynthesis of heparin in mammalians and the properties of this product have been described by Lindahl et al. in Lane D. and Lindahl U. (Eds.) "Heparin-Chemical and Biological Properties; Clinical Applications" Edward Arnold, London, 1986, 159-190 and Lindahl U. et al., TIBS, 1986, 11, 221-225.

The sequence formed by the pentasaccharide region of linkage for Antithrombin III (ATIII) named active pentasaccharide

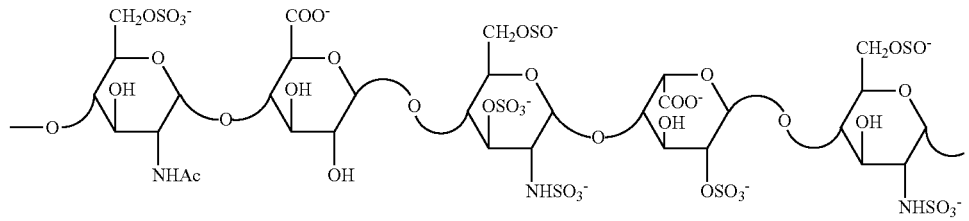

(J. Choay et al., Ann. N.Y. Acad. Sci., 1981, 376, 644-649), that is the structure needed for the high affinity binding of heparin to ATIII, is fundamental for heparin activity. This sequence contains one glucosamine unit sulfated in position 3, that is not normally present in the other parts of the heparin chain. Beside the activity through ATIII, heparin exerts its anticoagulant and antithrombotic activity through the activation of heparin cofactor II (HCII) and a selective inhibition of thrombin. It is known that the minimum saccharidic sequence necessary for HCII activation is a chain containing at least 24 monosaccharides (Tollefsen D. M. Seminars in Thrombosis and Hemostasis, 1990, 16, 66-70).

Heparin is a leading, widely used medicament for treating vascular disorders such as deep vascular thrombosis, or to prevent thrombosis (see Lassen M. R. et al., "Efficacy and safety of prolonged thromboprophylaxis with a low molecular weight heparin (Dalteparin) after total hip arthroplasty" Thrombosis Research, 1998, 89, 281-287 and, more recently, Motsch J. et al. "Update in the prevention and treatment of deep vein thrombosis and pulmonary embolism" Current Opinion in Anesthesiology, 2006, 19, 52-58), but it is subjected to drawbacks due to its extraction from bovine or porcine tissues, in particular to the risk of the presence of viruses or prions (as set forth in U.S. Pat. No. 5,958,899) or of other toxic glycosaminoglycans which can induce severe, even lethal, effects in patients under heparin anticoagulant treatment (Guerrini M. et al., Nat. Biotechnol., 2008, 26, 669-675). Hence, there is an extreme need of a medicament having the same biologic characteristics as heparin without the potential drawbacks thereof.

DESCRIPTION OF THE PRIOR ART

It is known that the capsular polysaccharide K5 isolated from the strain of *Escherichia coli*, described by Vann W. F. et al. in European Journal of Biochemistry, 1981, 116, 359-364 shows the same sequence of heparin and heparan sulfate precursor (N-acetylheparosan), namely a mixture of chains constituted by repeating disaccharide glucoronyl-β-1→4-glucosamine structures. This compound was chemically modified as described by Lormeau et al. in the U.S. Pat. No. 5,550,116 (Lormeau) and by Casu et al. in Carbohydrate Research, 1994, 263, 271-284 (Casu 1994) or chemically and enzymatically modified in order to obtain N,O-sulfated glycosaminoglycans, showing in vitro biological activities in coagulation of the same type of heparin as extracted from animal organs.

However, Lormeau and Casu 1994 disclose N,O-sulfated K5 polysaccharides consisting of disaccharide units formed by glucuronic acid and glucosamine units only (even though Casu 1994 supposed the presence of a little amount of a not better identified iduronic units in a subfraction), namely of products which do not have the same structure, in particular they do not contain iduronic acid units. These products cannot possess anticoagulant/antithrombotic properties similar to those of heparin because they do not contain the active pentasaccharide which is responsible of the heparin anticoagulant/antithrombotic activity on all the coagulation parameters. In addition, all the non-epimerized compounds have a different conformation and backbone in respect of the epimerized ones and of heparin. By consequence, all of these products are much less active than heparin and show a very low Anti-Xa/aPTT ratio as we demonstrated in Casu 1994.

The chemical and enzymatic modification of polysaccharide K5 was described for the first time in IT 1230785, wherein the polysaccharide K5 (hereinbelow also simply referred to as "K5") is submitted to (a) a N-deacetylation and a N-sulfation; (b) an enzymatic C5-epimerization of the glucuronic units; (c) a 2-O and/or 6-O-sulfation; and (d) an optional enzymatic 3-O-sulfation, but this method does not give products having a satisfactory activity in respect of that of heparin as extracted from animal organs, hereinafter referred to as "commercial heparin" or "standard heparin", the latter expression designating the fourth International Standard of heparin.

WO 92/17507 discloses a method for preparing heparin-like products starting from K5 by (a) N-deacetylation and N-sulfation, (b) C5 epimerization, and (c) O-sulfation, step (c) being optionally followed by a N-resulfation. According to this method, the amount of iduronic acid of the resulting product is low (about 20% of the global content of uronic acids).

WO 96/14425 and U.S. Pat. No. 5,958,899 disclose an improved method for the preparation of heparin-like products having a high iduronic acid content, starting from K5, by (a) N-deacetylation and N-sulfation, (b) epimerization by a C5 epimerase, and (c) sulfation of at least some free hydroxy groups, step (b) being conducted under controlled conditions. This method for the first time provided a N-sulfate, C5-epimerized K5 polysaccharide starting material having an iduronic acid content of from 40% to 60%, but affords products which lack a considerable amount of N-sulfate groups, lost during the O-sulfation. In addition, according to this method the C5 epimerization is carried out in a reaction medium consisting of a classical buffer solution at pH 7.4 constituted by HEPES, potassium chloride and EDTA to which TRITON X-100 and an additive or more additives in an amount suitable to increase the viscosity of said buffer solution.

WO 97/43317 and U.S. Pat. No. 6,162,797 disclose derivatives of K5 having high anticoagulant activity which are prepared by submitting K5 to (a) N-deacetylation and N-sulfation, (b) C5 epimerization, (c) O-sulfation of the epimerized product, previously transformed in a salt thereof with an organic base, and dialysis, and (d) N-resulfation. The products obtained according to this method exhibit a very high global anticoagulant activity.

WO 98/42754 and U.S. Pat. No. 6,197,943 disclose glycosaminoglycans having high antithrombotic activity in vitro, containing at least 20% of iduronic units sulfated in position 2 and not sulfated in position 3 and at least 30% of sulfaminoglucosaminic units sulfated in position 3 and in position 6, and having a sulfates/carboxyls molar ratio ranging from 2.0 to 3.5. These glycosaminoglycans are prepared by a method comprising a) preparation of the salt of an organic base of the starting supersulfated glycosaminoglycan; b) partial solvolytic desulfation of the salt of the organic base of the step a); c) N-resulfation of the partially desulfated product of the step b); d) possible 6-O-resulfation of the product of the step c). The products obtained according to this method have the disadvantage of lacking either O-sulfate groups when the optional O-resulfation step (f) is not performed, or N-sulfate groups, which are lost when step (f) is performed. In fact, the described method provides either an N-sulfation of an O-desulfated product or the O-sulfation (not described) of an N-sulfated glycosaminoglycan. Thus, the incomplete N- or O-sulfation, especially the incomplete 6-O-sulfation (always below 60%), as shown in Table 3, column 4 and in Table 4, row 10 (Example 16, epiK5 polysaccharide derivative), involves, in the case of C5-epimerized K5 polysaccharide, very low anti-Xa values, thus giving a very low anti-Xa/aPPT ratio, as shown in Table 4, Examples 14-17 concerning derivatives of K5 polysaccharide, in particular Example 16, concerning a derivative of epiK5 polysaccharide having an anti-Xa/aPPT ratio lower than 0.3.

In summary, the prior art does not disclose any C5 epimerized product derived from K5 polysaccharide which is active on all the anticoagulant/antithrombotic parameters on which heparin is active, in particular on the Anti-Xa, Anti-IIa, aPTT, HCII and ATIII-affinity parameters, coupled with an Anti-Xa/aPTT ratio higher than that of extractive heparin. According to the disclosures of all the above-cited documents, except the direct derivatives of extractive heparin (but no evidence of their activity on all the coagulation parameters is given in said documents) none of the products described by the prior art present characteristics allowing the replacement of heparin for a use in mammals' anticoagulant/antithrombotic therapy.

SUMMARY OF THE INVENTION

We improved the above-mentioned, known processes, providing a C5 epimerization of N-sulfate K5 polysaccharide. by carrying out said C5-epimerization in the presence of bivalent cations such as $Ba^{++}$, $Ca^{++}$, $Mg^{++}$ and $Mn^{++}$, instead of organic polymers such as TRITON X-100, thus obtaining the same degree of epimerization as that described in WO 96/14425 and U.S. Pat. No. 5,958,899 by a simpler and, hence, more attractive method.

We have also found that K5 polysaccharide may be submitted to a six-step process, carried out in a precise sequence, which allows the preparation of new glycosaminoglycans characterized by a high activity in all the coagulation parameters, said activity being extremely high on the Heparin Cofactor II (HCII) and antithrombin (Anti-IIa) parameters, thus being excellent candidates to the replacement of extractive heparin.

Thus, we have found new glycosaminoglycans derived from K5 polysaccharide from *Escherichia coli* with a molecular weight from 3,000 to 30,000, containing from 25% to 50% by weight of the chains with high affinity for ATIII and with a high anticoagulant and antithrombotic activity which is comprised between 1.5 and 4 if the results are expressed as ratio HCII/Anti-Xa activities with a prevalence of the activities which involve thrombin inhibition.

Said glycosaminoglycans are synthesized through a process comprising some steps of chemical and enzymatic modification and characterized by a step of epimerization from D-glucuronic acid to L-iduronic acid using the enzyme glucuronosyl C5 epimerase in solution or in immobilized form in presence of specific divalent cations, said enzyme being chosen from the group including recombinant glucuronosyl C5 epimerase, glucuronosyl C5 epimerase from murine mastocytoma and glucuronosyl C5 epimerase extracted from bovine liver and said divalent cations being chosen from the group comprising Ba, Ca, Mg and Mn.

More particularly, the process for the preparation of said glycosaminoglycans comprises the following steps: (i) N-deacetylation/N-sulfation of the polysaccharide K5, (ii) partial C-5 epimerization of the carboxyl group of the glucuronic acid moiety to the corresponding iduronic acid moiety, (iii) oversulfation, (iv) selective O-desulfation, (v) selective 6-O-sulfation, and (vi) N-sulfation.

We have also found that different compounds are obtained by modulating the reaction time of the selective O-desulfation.

Moreover, we have found that, by carrying out the O-desulfation of the product obtained at the end of step (iii), whenever prepared according to the steps (i)-(iii), for a period of time of from 135 to 165 minutes, new compounds are obtained which show the best antithrombotic activity and a bleeding potential lower than that of any other heparin-like glycosaminoglycan.

It has particularly been found that new glycosaminoglycans having a very high antithrombin activity and a bleeding potential lower than that of heparin may be obtained by a process which sequentially comprises (i) N-deacetylation/N-sulfation of the polysaccharide K5, (ii) partial C-5 epimerization of the carboxyl group of the glucuronic acid moiety to the corresponding iduronic acid moiety, (iii) oversulfation, (iv) time and temperature controlled selective O-desulfation, (v) 6-O-sulfation, (vi) N-sulfation, and also comprises an optional depolymerization step at the end of one of steps (ii)-(vi). Due to this reactions' sequence, these novel glycosaminoglycans are almost completely N-sulfated and highly 6-O-sulfated, thus being different from those obtained by the previously described methods, in particular in WO 98/42754/U.S. Pat. No. 6,197,943, thus showing an antiXa activity of the same order and even higher than that of extractive heparin and an aPTT activity lower than that of extractive heparin, such that they show very favorable HCII/AntiXa and Anti-Xa/aPTT ratios.

More particularly, it has surprisingly been found that, if in step (iv) of the above process the selective O-desulfation of the product obtained at the end of step (iii) is carried out in a mixture dimethyl sulfoxide (DMSO)/methanol for a period of time of from 135 to 165 minutes, preferably of about 150 minutes, at a temperature of 50-70° C., new glycosaminoglycans of heparin-type are obtained, said glycosaminoglycans having an anti-Xa activity at least of the same order of standard heparin and a global anticoagulant activity, expressed for example as aPTT, lower than that of standard heparin, a Heparin Cofactor II (HCII) activity at least as high as that of standard heparin and an anti-IIa (antithrombin) activity much higher than that of standard heparin, said novel glycosaminoglycans also having a reduced bleeding risk in respect of commercial heparin.

Furthermore, it has been found that by carrying out step (iv) under the above-illustrated conditions, the biological activity with low bleeding risk of the compound obtained at the end of step (vi) is maintained after depolymerization, said activity of the depolymerized product being expressed by a very high antithrombin activity, anti-Xa and HCII activities of the same order as that of standard heparin and a global anticoagulant activity, measured as aPTT potency, lower than that of standard heparin. Thus, by carrying out step (iv) under these controlled conditions, it is possible to overcome the abovementioned disadvantages of the known processes and to obtain new glycosaminoglycans, having improved and selective antithrombin activity, useful as specific coagulation-controlling and antithrombotic agents.

Herein below, derivatives of polysaccharide K5 are also referred to as "deacetylated K5" for N-deacetylated K5 polysaccharide, "N-sulfate K5" for N-deacetylated, N-sulfated K5 polysaccharide, "C5-epimerized N-sulfate K5" for C5 epimerized, N-deacetylated, N-sulfated K5 polysaccharide, "C5-epimerized N,O-sulfate K5" for C5 epimerized, N-deacetylated, N,O sulfated K5 as obtained at the end of step (vi) above, with or without depolymerization. Unless otherwise specified, starting K5 polysaccharide and its derivatives are intended in form of their sodium salts.

DETAILED DESCRIPTION OF THE INVENTION

The present invention relates to glycosaminoglycans derived from K5 polysaccharide from *Escherichia coli* (further simply named K5), obtained by a process which includes the following steps:
(a) Preparation of K5 from *Escherichia coli*
(b) N-deacetylation/N-sulfation
(c) C5 epimerization
(d) Oversulfation
(e) Selective O-desulfation
(f) Selective 6-0 sulfation (optional)
(g) N-sulfation
The different steps of the process are detailed as follows.
(a) Preparation of K5 from *Escherichia coli*
First a fermentation in flask is performed according to the Italian patent application MI99A001465 (WO 01/02597) and using the following medium:

| Defatted soy | 2 g/l |
| --- | --- |
| K$_2$HPO$_4$ | 9.7 g/l |
| KH$_2$PO$_4$ | 2 g/l |
| MgCl$_2$ | 0.11 g/l |
| Sodium citrate | 1 g/l |
| Ammonium sulfate | 1 g/l |
| Glucose | 2 g/l |
| Water | 1,000 ml | pH 7.3

The medium is sterilized at 120° C. for 20 minutes. Glucose is prepared separately as a solution that is sterilized at 120° C. for 30 minutes and sterile added to the medium. The flask is inoculated with a suspension of *E. coli* cells Bi 8337/41 (O10:K5:H4) from a slant containing tryptic soy agar and incubated at 37° C. for 24 hours under controlled stirring (160 rpm, 6 cm of run). The bacterial growth is measured counting the cells with a microscope. In a further step, a Chemap-Braun fermentor with a volume of 14 liters containing the same medium above is inoculated with the 0.1% of the above flask culture and the fermentation is performed with 1 vvm aeration (vvm=air volume for liquid volume for minute), 400 rpm stirring and temperature of 37° C. for 18 hours. During the fermentation pH, oxygen, residual glucose, produced K5 polysaccharide and bacterial growth are measured.

At the end of the fermentation the temperature is raised to 80° C. for 10 minutes. The cells are separated from the medium by centrifugation at 10,000 rpm and the supernatant is ultrafiltrated through a SS316 (MST) module equipped with PES membranes with a nominal cut off of 800 and 10,000 D to reduce the volume to ⅕. Then K5 polysaccharide is precipitated adding 4 volumes of acetone at 4° C. and left to sediment for one night at 4° C. and finally is centrifuged at 10,000 rpm for 20 minutes or filtrated.

Then a deproteinization using a protease of the type II from *Aspergillus Orizae* in 0.1M NaCl and 0.15 M ethylenediaminotetracetic acid (EDTA) at pH 8 containing 0.5% sodium dodecyl sulfate (SDS) (10 mg/l of filtrate) at 37° C. for 90 minutes is performed. The solution is ultrafiltrated on a SS 316 module with a nominal cut off membrane of 10,000 D with 2 extractions with 1M NaCl and washed with water until the absorbance disappears in the ultrafiltrate. K5 polysaccharide is then precipitated with acetone and a yield of 850 mg/l of fermentor is obtained. The purity of the polysaccharide is measured by uronic acid determination (carbazole method), $^1$H- and $^{13}$C-NMR, UV and protein content. The purity is above 80%.

Figure 2:
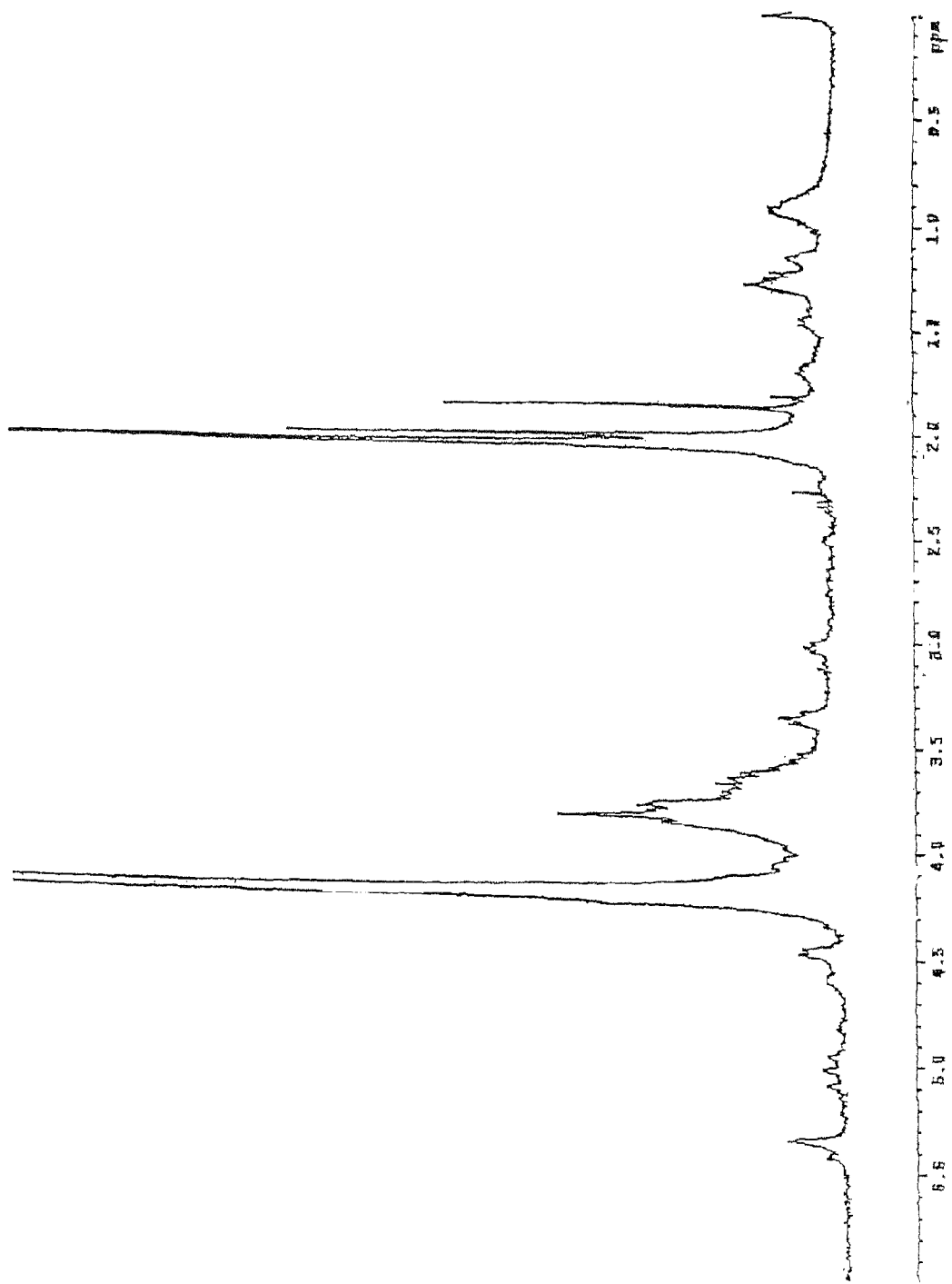
FIG. 2 shows the $^1$H-NMR spectrum of the starting K5 polysaccharide of Example 1 (a) and Example 12.

The so obtained polysaccharide is composed of two fractions with different molecular weight, 30,000 and 5,000 D respectively as obtained from the HPLC determination using a 75 HR Pharmacia column and one single fraction with retention time of about 9 minutes using two columns of Biosil SEC 250 in series (BioRad) and Na$_2$SO$_4$ as mobile phase at room temperature and flow rate of 0.5 ml/minute. The determination is performed against a curve obtained with heparin fractions with known molecular weight. The $^1$H-NMR is shown in FIG. 2. Such a K5 polysaccharide may be used as starting material for the process of the present invention because its purity is sufficient to perform said process. Advantageously, this starting material is previously purified. A suitable purification of K5 is obtained by treatment with Triton X-100.

Typically, Triton X-100 is added to a 1% aqueous solution of the already sufficiently pure, above K5 polysaccharide to a concentration of 5%. The solution is kept at 55° C. for 2 hours under stirring. The temperature is raised to 75° C. and during the cooling to room temperature two phases are formed. On the upper phase (organic phase) the thermic treatment with the formation of the two phases is repeated twice. The aqueous phase containing the polysaccharide is finally concentrated under reduced pressure and precipitated with ethanol or acetone. The organic phase is discarded. The purity of the sample is controlled by $^1$H-NMR and results to be 95%. The yield of this treatment is 90%.

(b) N-Deacetylation/N-Sulfation.

10 g of purified K5 are dissolved in 100-2,000 ml of 2N sodium hydroxide and left to react at 40-80° C. for the time necessary to achieve the complete N-deacetylation, which is never above 30 hours. The solution is cooled to room temperature and the pH brought to neutrality with 6N hydrochloric acid.

The solution containing the N-deacetylate K5 is kept at 20-65° C. and 10-40 g of sodium carbonate are added together with 10-40 g of a sulfating agent chosen among the available reagents such as the adduct pyridine.sulfur trioxide, trimethylamine.sulfur trioxide and the like. The addition of the sulfating agent is performed during a variable time till 12 hours. At the end of the reaction the solution is brought to room temperature, if necessary and to a pH of 7.5-8 with a 5% solution of hydrochloric acid.

The product is purified from salts with known technologies, for instance by diafiltration using a spirale membrane with 1,000 D cut off (prepscale cartridge—Millipore). The process is finished when the conductivity of the permeate is less than 1,000 µS, preferably less than 100 µS. The volume of the product obtained is concentrated till 10% polysaccharide concentration using the same filtration system as concentrator. If necessary the concentrated solution is dried with the known technologies. The N-sulfate/N-acetyl ratio ranges from 10/0 to 7/3 measured by $^{13}$C-NMR.

(c) C5 Epimerization.

The step of C5 epimerization according to the present invention can be performed with the enzyme glucuronosyl C5 epimerase (also called C5 epimerase) in solution or its immobilized form.

C5 Epimerization with the Enzyme in Solution.

From $1.2 \times 10^7$ to $1.2 \times 10^{11}$ cpm (counts per minute) of natural or recombinant C5 epimerase, calculated according to the method described by Campbell P. et al., Analytical Biochemistry, 1983, 131, 146-152 are dissolved in 2-2,000 ml of 25 mM Hepes buffer at a pH comprised between 5.5 and 7.4, containing 0.001-10 g of N-sulfate K5 and one or more of the ions chosen among barium, calcium, magnesium, manganese at a concentration ranging from 10 and 60 mM. The reaction is performed at a temperature ranging from 30 and 40° C., preferably 37° C. for 1-24 hours. At the end of the reaction the enzyme is inactivated at 100° C. for 10 minutes.

The product is purified by a passage on a diethylaminoethyl (DEAE)-resin or DEAF device Sartobind and unbound with 2M NaCl and finally desalted on a Sephadex G-10 resin or it is purified by precipitation with 2 volumes of ethanol and passage on a IR 120 H$^+$ resin to make the sodium salt.

The C5 epimerized N-sulfate K5 polysaccharide thus obtained shows an iduronic acid/glucuronic acid ratio between 40:60 and 60:40 calculated by $^1$H-NMR as already described in WO 96/14425. If the analyzed sample contains traces of divalent ions the peaks of iduronic acid can show a chemical shift in the $^1$H-NMR spectrum.

C5 Epimerization with Immobilized Enzyme.

Immobilization. The enzyme C5 epimerase, natural or recombinant, can be immobilized on different inert supports including resins, membranes or glass beads derivatized with reactive functional groups using the most common technologies of linkage for the enzymes such as cyanogen bromide, glutaraldehyde, carbodiimide or making the enzyme react with a ionic exchange resin or adsorbe on a membrane. According to the present invention the reactions of binding of the enzyme to the inert support are performed in presence of the substrate N-sulfate K5 to avoid the active site of the enzyme to link with loss of activity.

Measure of activity. The measure of the activity of the immobilized enzyme is performed according to Malmström et al. in J. Biol. Chem., 1980, 255, 3878-3883 by recirculating the amount of N-sulfated K5 that theoretically can be epimerized by that amount of cpm of immobilized enzyme onto a column of the immobilized enzyme in presence of 25 mM Hepes, 0.1M KCl, 0.01% Triton X-100 and 0.15 M EDTA pH 7.4 buffer at 37° C. overnight at a flow rate of 0.5 ml/minute. After the purification by DEAE chromatographic method and desalting on Sephadex G-10 the product is freeze dried and the content of iduronic acid is calculated by $^1$H-NMR.

The ratio iduronic acid/glucuronic acid shall be about 30/70.

Epimerization. A volume of 20-1,000 ml of 25 mM Hepes buffer at a pH between 6 and 7.4 containing one or more ions chosen among barium, calcium, magnesium, manganese at a concentration between 10 and 60 mM and 0.001-10 g N-sulfate K5 polysacccharide kept at a temperature between 30 and 40° C., are recirculated at a flow rate of 30-160 ml/hour for 1-24 hours in a column containing from $1.2 \times 10^7$ to $3 \times 10^{11}$ cpm equivalents of the enzyme immobilized on the inert support kept at a temperature from 30 to 40° C. At the end of the reaction the sample is purified with the same methods indicated in the epimerization in solution, i.e. by a passage on a diethylaminoethyl (DEAE)-resin or DEAE device Sartobind and unbound with 2M NaCl and finally desalted on a Sephadex G-10 resin or it is purified by precipitation with 2 volumes of ethanol and passage on a IR 120 H$^+$ resin to make the sodium salt in water solution.

The ratio iduronic acid/glucuronic acid of the C5 epimerized N-sulfate K5 polysaccharide thus obtained ranges between 40:60 and 60:40.

d) Oversulfation

The solution containing the epimerized product of step c) at a concentration of 10% is cooled at 10° C. and passed through an IR 120 H$^+$ column or equivalent (35-100 ml). Both the column and the container of the product are kept at 10° C. After the passage of the solution the resin is washed with deionized water until the pH of the flow through is more than 6 (about 3 volumes of deionized water). The acidic solution is brought to neutrality with a tertiary amine or quaternary ammonium base such as tetrabutylammonium hydroxide (15% aqueous solution) obtaining the ammonium salt of the polysaccharide. The solution is concentrated to the minimum volume and freeze dried. The product obtained is suspended in 20-500 ml of dimethyl formamide (DMF) or dimethyl sulfoxide (DMSO) and added with 15-300 g of a sulfating agent such as the adduct pyridine .SO$_3$ in the solid form or in solution of DMF or DMSO. The solution is kept at 20-70° C., preferably between 40 and 60° C. for 2-24 hours.

At the end of the reaction the solution is cooled to room temperature and added with acetone saturated with sodium chloride till complete precipitation. The precipitate is separated from the solvent by filtration, solubilized into the minimum amount of deionized water (for instance 100 ml) and added with sodium chloride to obtain a 0.2M solution. The solution is brought to pH 7.5-8 with 2N sodium hydroxide and added with acetone till complete precipitation. The precipitate is separated from the solvent by filtration. The solid obtained is dissolved into 100 ml of deionized water and purified from the residual salts by ultrafiltration as described in step (b).

Part of the product is freeze dried for the structural analysis of the oversulfated product by $^{13}$C-NMR. The content of sulfates per disaccharide of the product obtained is 2.0-3.5 calculated according to Casu B. et al., Carbohydrate Research, 1975, 39, 168-176. The position 6 of the glucosamine is sulfated at 80-95% and the position 2 is completely unsulfated. The other sulfate groups are present in position 3 of the amino sugar and 2 and 3 of the uronic acid. Thus, the obtained glycosaminoglycan is a C5-epimerized O-oversulfate K5 polysaccharide having its amino group in its free form.

(e) Selective O-Desulfation.

The solution containing the product of the step (d) is passed through a cationic exchange resin IR 120 H$^+$ or equivalent (35-100 ml). After the passage of the solution the resin is washed with deionized water till the pH of the flow through is more than 6 (about 3 volumes of deionized water). The acidic solution is brought to neutrality with an organic base such as pyridine. The solution containing the organic base salt of the oversulfated product of step (d) is concentrated to the minimum volume and freeze dried. The product obtained is treated with 20-2,000 ml of a solution of DMSO/methanol (9/1 V/V) and the solution is kept at 45-90° C. for 1-8 hours. Finally the solution is added with 10-200 ml of deionized water and treated with acetone saturated with sodium chloride to complete precipitation.

Figure 7:
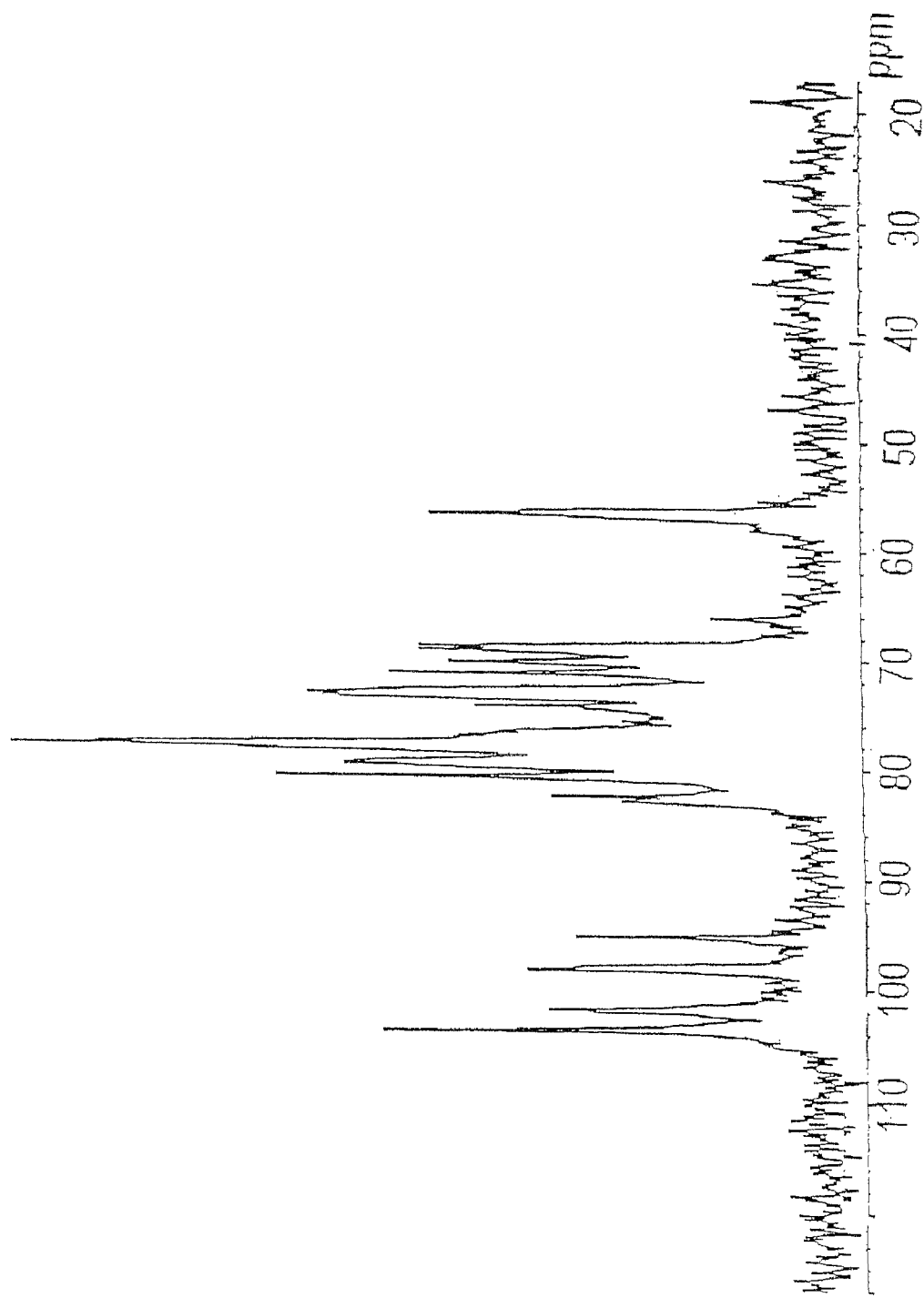
FIG. 7 shows the $^{13}$C-NMR spectrum of the oversulfate compound obtained in Example 1 (d).

With the selective O-desulfation the sulfate groups in position 6 of the glucosamine are eliminated first, then the sulfates in position 3 and 2 of the uronic acid and finally the sulfate in position 3 of the amino sugar. The extent of the selective, partial O-desulfation obviously depends on temperature and reaction time, the term "partial" being thus intended in the broadest range. In particular, according to a reaction time of from 1 to 8 hours at a given temperature (normally about 60° C.), the lost of sulfate groups may be of a low percent down to an almost complete desulfation. For example, from the oversulfated product characterized by the $^{13}$C-NMR spectrum of FIG. 7 showing a sulfation degree of 3.1-3.2, a partially desulfated product containing from 1% to 95% of the originally present sulfate groups may be obtained. In particular, from the cited oversulfated product, a partially desulfated, O-sulfated K5 polysaccharide having a sulfation degree of from 0.5 to 1.1 is obtained by carrying out the desulfation reaction for 2-4 hours at 60° C.

The solid obtained, a C5-epimerized O-sulfate K5 polysaccharide having its amino group in its free form is purified by diafiltration as described in step (b).

A portion of the sample is freeze dried for the structural analysis by $^{13}$C-NMR. If the content of the sulfate groups in position 6 of the amino sugar is more than 60%, calculated as described by Casu B. et al. in Arzneimittelforschung Drug Research, 1983, 33-1, 135-142, the step g) is performed. Otherwise the next step is performed.

(f) Selective 6-0 Sulfation (Optional).

The solution containing the product of step (e) is treated as described in step (d) to obtain the tertiary or quaternary ammonium salt, but performing the reaction at 20-25° C. The ammonium salt is suspended in 20-500 ml of DMF. The suspension is cooled to 0° C. and treated with an amount of sulfating agent such as the adduct pyridine.SO$_3$ calculated in function of the percentage of the sulfate in position 6 of the amino sugar to be inserted taking in account a minimum of 60% of 6-0 sulfation calculated as described above. The quantity of sulfating agent is comprised between two and ten equivalents of the hydroxyl groups to be sulfated. The sulfating agent is added one step or with several additions in a total time of 20 minutes.

The sulfating agent can be in powder or dissolved in a small amount of DMF. The solution is kept at 0-5° C. for 0.5-3 hours. The solution is then added with acetone saturated with sodium chloride in the right amount to complete the precipitation. The solid obtained is purified by diafiltration as described in step (b).

A small amount is freeze dried for the structural analysis by $^{13}$C-NMR. If the content of 6-0 sulfate groups calculated by NMR is less than 60%, step (f) is repeated.

(g) N-Sulfation

The solution obtained in step (f) or, if it is the case, in step (e), is treated as described in step (b) for the N-sulfation, i.e. by adding sodium carbonate to the solid obtained at the end of step (f), in water at 40° C., with in a single addition and the pyridine.SO$_3$ adduct in 10 minutes and isolating the N-deacetylated, N,O-sulfated, C5-epimerized.K5 polysaccharide thus obtained.

The product of the present invention obtained from step (d) to step (g) can be chemically depolymerized as described in WO 82/03627, preferably after step (g).

The glycosaminoglycans obtained by the process of the invention are characterized by $^1$H- and $^{13}$C-NMR and by biological tests like anti-Xa, aPTT, HCII, Anti-IIa and affinity for ATIII. Their sulfation degree is from about 2 to about 3.1.

The product obtained can be fractionated by chromatography on resin or ultrafiltration obtaining low molecular weight fractions from 2,000 to 8,000 D and high molecular fractions from 25,000 to 30,000 D or it can be depolymerized with controlled known technologies such as nitrous acid deamination as described in WO 82/03627.

The typical characteristics of molecular weight and biological activity of the glycosaminoglycans obtained by the process of the invention (TN-2018 UF and IN-2018 LMW) are indicated in Table 1 in comparison with unfractionated heparin (Fourth International Standard) and LMW heparin (First International Standard).

The molecular weight is calculated as indicated in references. The molecular weights can be different from those of the starting polysaccharide due to the reaction conditions of the process of the invention.

The activities indicated in rows 1, 2, 3 and 4 are relative values in comparison with heparin taken as 100. The data of column 5 and 6 represent the range of values for the products prepared according to the process of the present invention.

TABLE 1

Biological activity of the product obtained by the described process

| | Sample | Unfractionated heparin (4$^{th}$ int. Standard) | LMW heparin (1$^{st}$ int. Standard) | IN-2018 UF | IN-2018 LMW |
|---|---|---|---|---|---|
| 1 | Anti Xa | 100 | 84 | 70-250 | 40-100 |
| 2 | APTT | 100 | 30 | 40-90 | 25-80 |
| 3 | HCII | 100 | n.d. | 300-500 | 100-200 |
| 4 | Anti IIa | 100 | 33 | 100-600 | 20-210 |
| 5 | Mean molecular weight | 13,500 | 4,500 | 18,000-30,000 a) 10,000-20,000 b) | 4,000-8,000 |
| 6 | Affinity for ATIII | 32% | n.d. | 25-50 | 20-40 | n.d.: not determined

REFERENCES

1. Thomas D. P. et al., Thrombosis and Hemostasis, 1981, 45, 214 against the 4th International Standard of Heparin.
2. Andersson et al., Thrombosis Research, 1976, 9, 575 against the 4th International Standard of Heparin.
3. The test is performed mixing 20 µl of a solution of 0.05 PEU (Plasma Equivalent Unit)/ml of HCII (Stago) dissolved in water with 80 µl of a solution of the sample under examination at different concentrations and 50 µl of Thrombin (0.18 U/ml-Boheringer) in 0.02M tris buffer pH 7.4 containing 0.15 M NaCl and 0.1% PEG-6,000. The solution is incubated for 60 seconds at 37° C., then 50 µl of 1 mM chromogenic substrate Spectrozyme (American Diagnostic) are added. The reaction is continuously recorded for 180 seconds with determinations every second at 405 nm using an automatic coagulometer ACL 7000 (Instrumentation Laboratory).
4. Test is performed mixing 30 µl of a solution containing 0.5 U/ml of ATIII (Chromogenix) dissolved in 0.1M tris buffer pH 7.4 with 30 µl of a solution of the sample under examination at different concentrations and 60 µl of thrombin (5.3 nKat (Units of Enzymatic Activity)/ml-Chromogenix) in 0.1 M tris buffer pH 7.4. The solution is incubated for 70 seconds at 37° C., then 60 µl of 0.5 mM chromogenic substrate S-2238 (Chromogenix) in water are added. The reaction is continuously recorded for 90 seconds with determinations every second at 405 nm using an automatic coagulometer ACL 7000 (Instrumentation Laboratory).
5. Harenberg and De Vries J. Chromatography, 1983, 261, 287-292
a) using a single column (Pharmacia 75HR)
b) using two columns (BioRad Bio-sil SEC250)
6. Höök M. et al., FEBS Letters, 1976, 66, 90-93

From the table it is evident that the product obtained with the present process shows comparable activity to the extractive heparin in the anti-Xa test (1) and reduced global anticoagulant activity (2) while the values of the tests which implies inhibition of thrombin are markedly higher (3,4). These characteristics are predictive of higher antithombotic properties and less side effects such as the bleeding effect of the product obtained compared to the extractive heparin, with the further advantage of being obtained by semisynthetic route and, hence, not subjected to the well-known drawbacks of extractive heparin, in particular to the risk of the presence of contaminants.

Due to their characteristics the glycosaminoglycans of the present invention can be used alone or in combination with acceptable pharmaceutical excipients or diluents, for the anticoagulant and antithrombotic treatment.

In consequence the present invention also comprises the compositions containing a suitable amount of said glycosaminoglycans in combination with pharmaceutically acceptable excipients or diluents.

Finally the present invention refers to the effective amount of said glycosaminoglycans for the anticoagulant and antithrombotic treatment.

According to an advantageous method, in a process for the preparation of K5 glycosaminoglycans comprising the steps (i)-(vi) above it is possible to modulate the activity of the obtained final compound by controlling the reaction time of step (iv), at a given temperature.

Thus, more particularly, the present invention provides a process for the preparation of K5 glycosaminoglycans comprising the steps of (i) N-deacetylation/N-sulfation of the polysaccharide K5, (ii) partial C-5 epimerization of the carboxyl group of the glucuronic acid moiety to the corresponding iduronic acid moiety, (iii) oversulfation, (iv) selective O-desulfation, (v) optional selective 6-O-sulfation, and (vi) N-sulfation, in which step (iv) comprises treating the oversulfated product obtained at the end of step (iii) with a mixture methanol/dimethyl sulfoxide for a period of time of from 135 to 165 minutes.

Preferably, said period of time is of about 150 minutes

The product of the present invention obtained from step (ii) to step (vi) can be chemically depolymerized as described in WO 82/03627, preferably after step (vi).

According to a preferred embodiment, the treatment of the oversulfated product obtained at the end of step (iii) with a mixture methanol/dimethyl sulfoxide is made for a period of time of about 150 minutes at a temperature of about 60° C.

According to this advantageous method, from the oversulfated products prepared according to steps (i)-(iii) new glycosaminoglycans are obtained which show the best antithrombotic activity and a bleeding potential lower than that of any other heparin-like glycosaminoglycan.

Particularly interesting K5 glycosaminoglycans are obtained according to this advantageous method if, in addition, the partial epimerization of step (ii) gives at least 40% of iduronic acid moiety, the oversulfation of step (iii) is carried out in an aprotic solvent at a temperature of 40-60° C. for 10-20 hours and step (v) of selective 6-O-sulfation is actually performed.

Thus, it is a further object of the present invention to provide a process for the preparation of novel glycosaminoglycans, which comprises
(i) reacting K5 polysaccharide with a N-deacetylating agent, then treating the N-deacetylated product with a N-sulfating agent;
(ii) submitting the N-sulfate K5 polysaccharide thus obtained to a C5-epimerization by glucuronosyl C5 epimerase to obtain a C5-epimerized N-sulfate K5 polysaccharide in which the iduronic/glucuronic ratio is from 60/40 to 40/60;
(iii) converting the C5-epimerized N-sulfate K5 polysaccharide, having a content of 40 to 60% iduronic acid over the total uronic acids, into a tertiary or quaternary salt thereof, then treating the salt thus obtained with an O-sulfating agent in an aprotic polar solvent at a temperature of 40-60° C. for 10-20 hours;
(iv) treating an organic base salt of the O-oversulfated K5 polysaccharide in its free amine form thus obtained with a mixture dimethyl sulfoxide/methanol at 50-70° C. for 135-165 minutes;
(v) treating a salt with an organic base of the partially O-desulfated product thus obtained with an O-sulfating agent at a temperature of 0-5° C. to obtain a 6-O-sulfation;
(vi) treating the product thus obtained with a N-sulfating agent;
whatever product obtained at the end of one of steps (ii) to (vi) being optionally submitted to a depolymerization.

The K5 polysaccharide used as starting material may be whatever product as obtained by fermentation of wild or cloned K5 producing *Escherichia coli* strains. In particular, one of the above-mentioned K5 may be employed, advantageously one of those illustrated by M. Manzoni et al. in Journal Bioactive Compatible Polymers, 1996, 11, 301-311 or in WO 01/02597, preferably previously purified.

Advantageous K5 starting materials have a low molecular weight, particularly with a distribution from about 1,500 to about 15,000, advantageously from about 2000 to about 9,000 with a mean molecular weight of about 5,000, or a higher molecular weight, particularly with a distribution from about 10,000 to about 50,000, advantageously from about 20,000 to about 40,000 with a mean molecular weight of about 30,000. Preferably, starting K5 has a molecular weight distribution from about 1,500 to about 50,000, with a mean molecular weight of 20,000-25,000. All the molecular weights are expressed in Dalton (D). The molecular weight of K5 and of its derivatives described herein below is intended as calculated by using heparin fractions having a known molecular weight as standards.

In step (i), the starting K5 is submitted to a N-deacetylation and subsequent N-sulfation which are carried out by methods known per se, i.e by deacetylating the K5 polysaccharide, preferably pure at least at 90%, in alkaline medium such as with aqueous sodium hydroxide, neutralizing the solution containing the N-deacetylated K5 polysaccharide for example with hydrochloric acid, treating it with a sulfating agent such as a trialkylamine.SO$_3$ or pyridine.SO$_3$ adduct in the presence of sodium carbonate, and isolating the N-deacetylate, N-sulfate K5 polysaccharide thus obtained, in particular as illustrated above for step (b) of N-deacetylation/N-sulfation.

Step (ii) may be performed with the enzyme glucuronosyl C5 epimerase (also called C5 epimerase) in solution or its immobilized form, in particular as set forth above for step (c) of C5 epimerization. According to a preferred embodiment, said C5 epimerization is performed with the enzyme in its immobilized form and comprises recirculating 20-1,000 ml of a solution of 25 mM Hepes at pH of from 6 to 7.4 containing 0.001-10 g of N-deacetylated N-sulfated K5 and one of said cations at a concentration between 10 and 60 mM through a column containing from $1.2 \times 10^7$ to $3 \times 10^{11}$ cpm of the immobilized enzyme on an inert support, said pH being about 7 and said C5 epimerization being performed at a temperature of about 30° C. by recirculating said solution with a flow rate of from 30 to 220 ml/hour, preferably of about 200 ml/hour for a time of about 24 hours, when the enzyme is a recombinant one.

Step (iii), consisting of an O-oversulfation, is carried out by previously converting the C5 epimerized N-sulfate K5 into a tertiary or quaternary salt thereof and then by treating said salt with an O-sulfating agent at a temperature of 40-60° C. for 10-20 hours. Typically, the solution containing the epimerized product of step (ii) at a concentration of 10% is treated as illustrated above for step (d) of oversulfation, in particular by heating a solution of the above salt in DMF or DMSO at 20-70° C. for 2-24 hours, preferably at 40-60° C. for 15-20 hours.

Part of the product obtained is freeze dried for the structural analysis of the oversulfated product by $^{13}$C-NMR. The content of sulfates per disaccharide of the product obtained is 2.8-3.5 calculated according to Casu B. et al., Carbohydrate Research 1975, 39, 168-176. The position 6 of the glucosamine is sulfated at 80-95% and the position 2 is completely unsulfated. The other sulfate groups are present in position 3 of the amino sugar and in positions 2 and 3 of the uronic acid.

Step (iv), consisting of a selective O-desulfation, is the key step of the process of the present invention, because it allows the preparation, at the end of step (vi), of glycosaminoglycans that, after depolymerization, give low molecular weight products substantially maintaining a high antithrombin activity. Typically, the solution containing the product of step iii) is passed through a cationic exchange resin IR 120 H$^+$ or equivalent (35-100 ml). After the passage of the solution, the resin is washed with deionized water till the pH of the flow through is more than 6 (about 3 volumes of deionized water). The acidic solution is brought to neutrality with pyridine. The solution is concentrated to the minimum volume and freeze dried. The product obtained is treated with 20-2,000 ml of a solution of DMSO/methanol (9/1 V/V) and the solution is kept at 50-70° C. for 135-165 minutes, preferably at about 60° C. for about 150 minutes. Finally the solution is added with 10-200 ml of deionized water and treated with acetone saturated with sodium chloride to complete the precipitation.

By the selective O-desulfation, sulfate groups in position 6 of the glucosamine are eliminated first, then the sulfate groups in position 3 and 2 of the uronic acid and finally the sulfate group in position 3 of the amino sugar. The $^{13}$C-NMR spectrum of the sample obtained (FIG. 14) shows the complete N-desulfation of the glucosamine residue (signal at 56 ppm) and the almost complete 6-O desulfation with the decreasing of the signal at 67.6 ppm and the appearance of the signal at 62.2 ppm. The signals at 65 and 86 ppm show the 2-O sulfated iduronic acid and the 3-O sulfated glucuronic acid respectively. The solid obtained is purified by diafiltration according to known methods, for instance by using a spiral membrane with 1,000 D cut off (prepscale cartridge—Millipore). The process is finished when the conductivity of the permeate is less than 1,000 µS, preferably less than 100 µS. The volume of the product obtained is concentrated till 10% polysaccharide concentration using the same filtration system as concentrator. If necessary, the concentrated solution is dried by conventional technologies.

Step (v), consisting of a 6-O-sulfation, must also be carried out if, after a depolymerization step following step (vi) below, compounds having a high antithrombin activity, anti-Xa, HCII activities as high as those of heparin and a low aPTT are desired. The selective 6-O-sulfation is carried out by converting the selectively O-desulfated product into a tertiary or quaternary salt thereof and treating said salt with an O-sulfating agent at low temperature, more particularly at 0-5° C. for 0.5-3 hours. Typically, the 6-O-sulfation is carried out as illustrated above for step (0 of O-sulfation. The solid obtained is purified by diafiltration as described in step (iv). A small amount is freeze dried for the structural analysis by $^{13}$C-NMR. If the content of 6-O sulfate groups calculated by NMR, as described by Casu et al. in Arzneimittel-Forschung Drug Research, 1983, 33, 135-142, is less than about 85%, step (v) is repeated.

Step (vi) must be performed, according to known methods, because a non-negligible percent, up to 100%, of N-sulfate groups is lost during the O-oversulfation step. Thus, a solution of the product obtained in step (v) is treated as described in step (i) for the N-sulfation, i.e. by adding sodium carbonate to the solid obtained at the end of step (v), in water at 40° C. in a single addition, and the pyridine.SO$_3$ adduct in 10 minutes, in order to isolate the C5-epimerized N,O-sulfate K5 polysaccharide of the invention.

Without the 6-O-sulfation before the N sulfation, the final C5-epimerized N,O-sulfate K5 polysaccharide lacks an important percentage of 6-O-sulfate groups and, if said 6-O-sulfation is carried out after an N-sulfation, a non-negligible part of the existing N-sulfate groups are lost, such that said final product has a unfavorable Anti-Xa/aPTT ratio, much lower than that of extractive heparin.

Whatever high molecular weight product obtained at the end of one of steps (ii) to (vi) may be chemically depolymerized in order to obtain, as final products, low molecular weight glycosaminoglycans having high antithrombin activity, anti-Xa and HCII activities even of the same order, and even higher in the case of HCII activity, in respect of those of standard heparin and an aPTT activity lower than that of standard heparin. This activity profile is unexpected because low molecular weight glycosaminoglycans obtained according to a process involving steps (i)-(vi), in which step (iv) is carried out under not controlled time conditions, said process being followed by a depolymerization, showed an even severe lowering of all of the biological activities, as it happens in the case of the depolymerization of heparin, which usually leads to products with a severe lowering of all the anticoagulant parameters, especially of the anti-IIa and HCII activities.

Generally, the process of the present invention is performed by carrying out steps (i)-(vi) sequentially and submitting the high molecular weight, C5-epimerized N,O-sulfate K5 obtained at the end of step (vi) to depolymerization. Of course, such a depolymerization is not necessary to prepare a low molecular weight C5-epimerized N,O-sulfate K5 if, as starting material, a low molecular weight fraction of K5, optionally previously purified, is used as starting material.

The depolymerization may be carried out according to the known methods for the depolymerization of heparin, for example by nitrous acid and subsequent reduction with sodium borohydride (WO 82/03627-EP 37319), by sodium periodate (EP 287477), by free radicals (EP 121067) or by β-elimination (EP 40144), in order to obtain, as final product, a glycosaminoglycan constituted by a mixture of chains in which at least 80% of said chains have a molecular weight distribution ranging from about 2,000 to about 10,000 with a mean molecular weight of from about 4,000 to about 8,000.

The glycosaminoglycans obtained by the process of the invention are characterized by $^1$H- and $^{13}$C-NMR and by biological tests like anti-Xa, aPTT, HCII, Anti-IIa and affinity for ATIII. As already mentioned above, the sulfation degree, namely the number of sulfate groups per disaccharide unit expressed as sulfate/carboxyl ratio ($SO_3^-/COO^-$), is determined as described by Casu et al., Carbohydrate Research, 1975, 39, 168-176.

The product obtained at the end of step (vi), without any depolymerization, may also be fractionated by chromatography on resin or ultrafiltration to obtain low molecular weight fractions of from 2,000 to 8,000 D and high molecular weight fractions of from 25,000 to 30,000 D.

The novel C5 epimerized N,O-sulfate K5 glycosaminoglycans obtained at the end of the process of the present invention are generally isolated in form of their sodium salt. Said sodium salt may be converted into another salt. Said other salt may be another alkaline metal salt or an alkaline-earth metal, ammonium, tri($C_1$-$C_4$)alkylammonium, tetra($C_1$-$C_4$)alkylammonium, aluminum or zinc salt.

The products obtained by the process of the present invention show comparable activity to the extractive heparin in the anti-Xa test and reduced global anticoagulant activity (aPTT method) while the values of the tests involving inhibition of thrombin, heparin cofactor II (HCII) and anti-IIa activities are of the same order as or markedly higher than those of standard heparin. These characteristics of the product obtained are predictive of better coagulation modulating and antithrombotic properties and lower side effects, such as bleeding effect, than those of commercial heparins and of other known anticoagulant glycosaminoglycans.

Thus it is a further object of the present invention to provide novel C5-epimerized N,O-sulfate K5 glycosaminoglycans obtainable by a process which comprises
(i) reacting K5 polysaccharide with a N-deacetylating agent, then treating the N-deacetylated product with a N-sulfating agent;
(ii) submitting the N-sulfate K5 thus obtained to a C5-epimerization by glucuronosyl C5 epimerase to obtain a C5-epimerized N-sulfate K5 polysaccharide in which the iduronic/glucuronic ratio is from 60/40 to 40/60;
(iii) converting the C5 epimerized N-sulfate K5, having a content of 40 to 60% iduronic acid over the total uronic acids, into a tertiary or quaternary salt thereof, then treating the salt thus obtained with an O-sulfating agent in an aprotic polar solvent at a temperature of 40-60° C. for 10-20 hours;
(iv) treating a salt with an organic base of the O-oversulfated product thus obtained with a mixture dimethyl sulfoxide/methanol at 50-70° C. for 135-165 minutes;
(v) treating a salt with an organic base of the partially O-desulfated product thus obtained with an O-sulfating agent at a temperature of 0-5° C.;
(vi) treating the product thus obtained with a N-sulfating agent;
whatever product obtained at the end of one of steps (ii) to (vi) being optionally submitted to a depolymerization and the sodium salt of the end product being optionally converted into another salt.

Particularly advantageous C5-epimerized N,O-sulfate K5 glycosaminoglycans are those obtainable by the above process, in which step (iv) is carried out in a 9/1 (V/V) dimethyl sulfoxide/methanol mixture at about 60° C. for about 150 minutes.

A preferred class of glycosaminoglycans derived from K5 is obtainable by performing steps (i)-(vi) above on a previously purified K5, whereby step (iv) is carried out by heating at about 60° C. in a 9/1 dimethyl sulfoxide/methanol mixture for about 150 minutes, and optionally submitting the C5-epimerized N,O-sulfate K5 thus obtained to a nitrous acid depolymerization and to a subsequent sodium borohydride reduction.

Advantageously, said other salt is another alkaline metal, an alkaline-earth metal, ammonium, tri($C_1$-$C_4$)alkylammonium, tetra($C_1$-$C_4$)alkylammonium, aluminum or zinc salt.

The C5-epimerized N,O-sulfate K5-glycosaminoglycans obtainable according to the process comprising steps (i)-(vi) above, including the optional depolymerization and salt formation, have the structure I as illustrated herein below.

Thus, it is another object of the present invention to provide novel glycosaminoglycans constituted by a mixture of chains in which at least 90% of said chains has the formula I

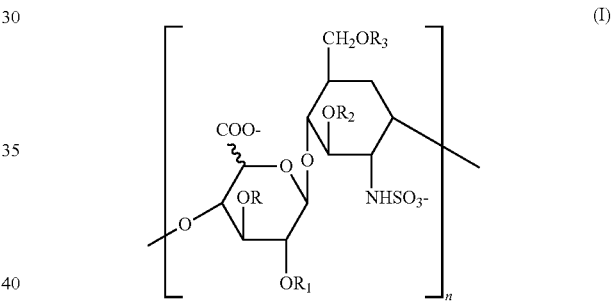

wherein 40-60% of the uronic acid units are those of iduronic acid, n is an integer of from 3 to 100, R, $R_1$, $R_2$ and $R_3$ represent a hydrogen atom or a $SO_3^-$ group and from about 65% to about 50% of R, $R_1$, $R_2$ and $R_3$ being hydrogen and the remaining being $SO_3^-$ groups distributed as follows $R_3$ is from about 85% to about 95% $SO_3$;
$R_2$ is from about 17 to about 21% $SO_3$;
$R_1$ is from about 15 to about 35% $SO_3^-$ in iduronic units and 0 to 5% $SO_3^-$ in glucuronic units;
R is from about 20 to about 40% $SO_3^-$ in glucuronic units and 0 to 5% in iduronic units;
the sum of the $SO_3^-$ percent in $R_1$, glucuronic units, and in R, iduronic units, is from 3 to 7%;

$R_1$ and R being not simultaneously $SO_3^-$ and being both hydrogen in 25-45% of the uronic acid units; the sulfation degree being from about 2.3 to about 2.9, and the corresponding cation being a chemically or pharmaceutically acceptable one.

In this context, the expression "chemically acceptable" is referred to a cation which is useful for the chemical syntheses, such as ammonium, tetra($C_1$-$C_4$)alkylammonium or tri($C_1$-$C_4$)alkylammonium ion, or for the purification of the products.

The compounds of formula I above show a very high antithrombin (Anti-IIa) activity (up to 3-5 times as high than that of extractive heparin), a favorable Anti-Xa/aPTT ratio in respect of heparin, thus being less inclined to induce bleeding in the anticoagulant/antithrombotic treatment of mammals, and also show a HCII/Anti-Xa ratio of from about 1 to about 3.

Advantageously, from about 60% to about 55% of R, $R_1$, $R_2$ and $R_3$ are hydrogen and the remaining are $SO_3^-$ groups for a sulfation degree of from about 2.4 to about 2.7.

Advantageous low molecular weight glycosaminoglycans are constituted by a mixture of chains in which at least 80% of said chains have the formula I wherein n is from 3 to 15.

Among these low molecular weight glycosaminoglycans, those in which said mixture of chains has a molecular weight distribution ranging from about 2,000 to about 10,000, with a mean molecular weight of from about 4,000 to about 8,000 are particularly advantageous.

Preferred glycosaminoglycans of this class is constituted by a mixture of chains with a mean molecular weight of from about 6,000 to about 8,000, in which at least 90% of said chains have the formula I above, wherein about 55% of the uronic acid units are those of iduronic acid and $R_3$ is from about 85% to about 90% $SO_3^-$; $R_2$ is about 20% $SO_3^-$; $R_1$ is from about 25% to about 30% $SO_3^-$ in iduronic units and 0 to about 5% $SO_3^-$ in glucuronic units; R is from about 30% to about 35% $SO_3^-$ in glucuronic units and in R, iduronic units, is about 5%; $R_1$ and R being not simultaneously $SO_3^-$ and being both hydrogen in from about 30% to about 40% of the uronic acid units; the sulfation degree being from about 2.5 to about 2.7, the corresponding cation being a chemically or pharmaceutically acceptable one.

A particularly preferred low molecular weight glycosaminoglycan of this class is constituted by a mixture of chains with a mean molecular weight of about 7,000, preferably of 7,400, in which at least 90% of said chains have the formula I above, wherein about 55% of the uronic acid units are those of iduronic acid and $R_3$ is about 85% $SO_3^-$;
$R_2$ is about 20% $SO_3^-$;
$R_1$ is about 25% $SO_3^-$ in iduronic units and 0 to about 5% $SO_3^-$ in glucuronic units;
R is about 30% $SO_3^-$ in glucuronic units and 0 to about 5% in iduronic units;
the sum of the $SO_3^-$ percent in $R_1$, glucuronic units and in R, iduronic units, is about 5%;

$R_1$ and R being not simultaneously $SO_3^-$ and being both hydrogen in about 40% of the uronic acid units; the sulfation degree being about 2.55, the corresponding cation being a chemically or pharmaceutically acceptable one.

These low molecular weight glycosaminoglycans, which are obtained by depolymerization of the final C5 epimerized, N,O-sulfate K5 polysaccharide of the process comprising steps (i)-(vi) above surprisingly maintain a high affinity for the active site of ATIII and, hence a significant activity on all the coagulation parameters. In particular, they show an Anti-Xa activity of the same order of and even equal to that of extractive heparin, an Anti-IIa (antithrombin) activity which is even much higher than that of extractive heparin, a HCII activity at least as high as standard heparin and a reduced global anticoagulant activity (aPTT), thus assuring a high anticoagulant/antithrombotic activity with a low risk of bleeding in the treatment of coagulation disorders or in the prevention or treatment of thrombosis.

Such surprising properties of the low molecular weight C5 epimerized, N,O-sulfate K5 polysaccharides obtained by 6-O-sulfation and N-sulfation of the partially O-desulfated C5 epimerized K5 polysaccharide, in its turn obtained by carrying out step (iv) for a period of time of from 135-165 minutes, i.e. for about 2.5 hours, may be only due to their affinity for ATIII, which is at least equal to that of extractive heparin. Thus, for unknown reasons, the fact of carrying out the partial O-desulfation reaction of step (iv) for a period of about 2.5 hours involves the formation of a percent of active pentasaccharide structure at least equal to that of extractive heparin. More particularly, these specific conditions unexpectedly generated an at least heparin-like percent of a 3-O sulfate glucosamine preceded by an unsulfated glucuronic acid and followed by a sulfated iduronic acid linked to an N-sulfate 6-O sulfate glucosamine (see the last paragraph of the above Background of The Invention). Of course, under the same reaction conditions, the higher is the percent of iduronic acid in the starting C5 epimerized N-sulfate K5 polysaccharide, the higher is the ATIII-affinity of the final low molecular weight C5 epimerized N,O-sulfate K5 polysaccharide.

The percent of the sulfate group in the 3-position of the glucuronic acid and 2-position of iduronic acid have been determined by $^{13}C$-NMR on the compound obtained after step (iv), by measuring the areas of the peaks at 86 and 65 ppm, attributable to the 3-O-sulfo-glucuronic acid unit and, respectively, to the 2-O-sulfo-iduronic acid unit and by considering that the percent of the added $SO_3$ groups in step (vi), in respect of the total amount of sulfate groups, is negligible.

Advantageous chemically and pharmaceutically acceptable cations are those derived from alkaline metals, alkaline-earth metals, ammonium, tri($C_1$-$C_4$)alkylammonium, tetra ($C_1$-$C_4$)alkylammonium, aluminum and zinc, sodium and calcium ions being particularly preferred.

Advantageous high molecular weight glycosaminoglycans are constituted by a mixture of chains in which at least 80% of said chains have the structure I wherein n is from 20 to 100.

Among these glycosaminoglycans, those in which said mixture of chains has a molecular weight distribution ranging from about 9,000 to about 60,000, with a mean molecular weight of from about 12,000 to about 30,000 are preferred.

A particularly preferred high molecular weight glycosaminoglycan of this class is constituted by a mixture of chains with a mean molecular weight of 14,000-16,000, in which at least 90% of said chains have the formula I above, wherein about 55% of the uronic acid units are those of iduronic acid and $R_3$ is from about 85% to about 90% $SO_3^-$;
$R_2$ is about 20% $SO_3^-$;
$R_1$ is from about 25% to about 30% $SO_3^-$ in iduronic units and 0 to about 5% $SO_3^-$ in glucuronic units;
R is from about 30% to about 35% $SO_3^-$ in glucuronic units and 0 to about 5% in iduronic units;
the sum of the $SO_3^-$ percent in $R_1$, glucuronic units and in R, iduronic units, is about 5%;

$R_1$ and R being not simultaneously $SO_3^-$ and being both hydrogen in from about 30 to about 40% of the uronic acid units; the sulfation degree being from about 2.5 to about 2.7, the corresponding cation being a chemically or pharmaceutically acceptable one.

The novel glycosaminoglycans obtainable by the process sequentially comprising steps (i)-(vi) above, including optional depolymerization and salt formation, in particular those constituted by a mixture of chains in which at least 90% of said chains has the formula I, in which R, $R_1$, $R_2$ and $R_3$ are as defined above and the corresponding cation being a chemically or pharmaceutically acceptable one, preferably a sodium or calcium ion, show interesting biological activities on the coagulation parameters. Particularly, said novel glycosaminoglycans exhibit anti-Xa and HCII activities at least of the same order of that of standard heparin, an anti-IIa (antithrombin) activity higher than that of standard heparin and a global anticoagulant activity (expressed as aPTT titre) lower than that of standard heparin. More particularly, said novel glycosaminoglycans show ratios anti-Xa/aPTT, HCII/aPTT and anti-IIa/anti-Xa of from 1.5 to 3 and a HCII/antiXa ratio of from 1 to 3.

Due to their characteristics, the glycosaminoglycans of the present invention may be used alone or in combination with acceptable pharmaceutical excipients or diluents, for the control of the coagulation and for the antithrombotic treatment, in particular for the prevention or for the treatment of thrombosis.

Therefore, it is a further object of the present invention to provide pharmaceutical compositions comprising, as an active ingredient, a pharmacologically active amount of a C5-epimerized N,O-sulfate K5 glycosaminoglycan obtainable according to the process wherein steps (i)-(vi) above, including the optional depolymerization and formation of a pharmaceutically acceptable salt are performed as illustrated above, in admixture with pharmaceutically acceptable excipients or diluents.

Preferably, the active ingredient is obtainable according to steps (i)-(vi) above, including pharmaceutically acceptable salt formation, starting from a previously purified K5 and carrying out step (iv) in dimethyl sulfoxide/methanol 9/1 (V/V) at about 60° C. for about 150 minutes, and submitting the C5-epimerized N,O-sulfate K5 obtained at the end of step (vi) to depolymerization. Preferably, the thus obtainable C5-epimerized N,O-sulfate K5 glycosaminoglycan active ingredient is in form of an alkaline metal, alkaline-earth metal, aluminum or zinc salt Particularly, the present invention provides pharmaceutical compositions comprising a pharmacologically effective amount of a glycosaminoglycan constituted by a mixture of chains in which at least 90% of said chains has the formula I above, wherein 40-60% of the uronic acid units are those of iduronic acid, n is an integer of from 3 to 100, R, $R_1$, $R_2$ and $R_3$ represent a hydrogen atom or a $SO_3^-$ group and from about 65% to about 50% of R, $R_1$, $R_2$ and $R_3$ being hydrogen and the remaining being $SO_3^-$ groups distributed as follows
  $R_3$ is from about 85% to about 95% $SO_3^-$;
  $R_2$ is from about 17% and about 21% $SO_3^-$;
  $R_1$ is from about 15 to about 35% $SO_3$ in iduronic units and 0 to 5% $SO_3^-$ in glucuronic units;
  R is from about 20 to about 40% $SO_3^-$ in glucuronic units and 0 to 5% in iduronic units;
  the sum of the $SO_3^-$ percent in R1, glucuronic units, and in R, iduronic units, is from 3 to 7%;
$R_1$ and R being not simultaneously $SO_3^-$ and being both hydrogen in 25-45% of the uronic acid units; the sulfation degree being from about 2.3 to about 2.9, and the corresponding cation being a pharmaceutically acceptable one, as an active ingredient, and a pharmaceutical carrier.

More particularly the above compositions are indicated for the treatment of coagulation disorders or for the prevention or treatment of thrombosis and, thus, they have the same indication as heparin, with the advantage of not being of animal origin.

In said pharmaceutical compositions, for intravenous, subcutaneous or topical use, said glycosaminoglycan active ingredient is present in an effective dose for the prevention or treatment of diseases caused by disorders of the coagulation system, such as arterial or venous thrombosis, for the treatment of haematomas or as coagulation controlling agents during surgical operations.

In preparations for intravenous or subcutaneous use, the glycosaminoglycan active ingredient is dissolved in water, if necessary in the presence of a buffer and the solution is introduced in vials or syringes under sterile conditions.

Unit doses of said pharmaceutical compositions contain from 5 to 100 mg advantageously from 20 to 50 mg of active ingredient dissolved in 0.1 to 2 ml of water.

In compositions for topical use, the glycosaminoglycan active ingredient is mixed with pharmaceutically acceptable carriers or diluents known in the art for the preparation of gels, creams, ointments, lotions or solutions to be sprayed. In said compositions, the glycosaminoglycan active ingredient is present in a concentration of from 0.01% to 15% by weight advantageously.

Advantageous pharmaceutical compositions comprise, as an active ingredient, a pharmacologically active amount of a glycosaminoglycan constituted by a mixture of chains of formula I, as illustrated above, in which the counter-ion is a pharmaceutically acceptable one, advantageously a cation selected from the group consisting of alkaline metal, alkaline-earth metal, aluminum and zinc ions, preferably the sodium or calcium ion, and a pharmaceutical carrier.

Among these advantageous glycosaminoglycans, those which contain at least 80% of chains of formula I wherein n is from 3 to 15 or from 20 to 100 are preferred active ingredients, those in which the mixture of chains has a molecular weight distribution ranging from about 2,000 to about 10,000, with a mean molecular weight of from about 4,000 to about 8,000 or a molecular weight distribution ranging from about 9,000 to about 60,000, with a mean molecular weight of from about 12,000 to about 30,000, being particularly preferred.

Particularly advantageous pharmaceutical compositions comprise, as an active ingredient, a glycosaminoglycan constituted by a mixture of depolymerized chains in which at least 90% of said chains have the formula I above, wherein 40-60% of the uronic acid units are those of iduronic acid, n is an integer of from 3 to 100, R, $R_1$, $R_2$ and $R_3$ represent a hydrogen atom or a $SO_3$ group, from about 65% to about 50% of R, $R_1$, $R_2$ and $R_3$ being hydrogen and the remaining being $SO_3^-$ groups distributed as follows
  $R_3$ is from about 85% to about 95%, preferably about 85%, $SO_3^-$;
  $R_2$ is from about 17 to about 21%, preferably about 20%, $SO_3^-$;
  $R_1$ is from about 15 to about 35%, preferably about 25%, $SO_3^-$ in iduronic units and 0 to about 5% $SO_3^-$ in glucuronic units;
  R is from about 20 to about 40% $SO_3^-$ in glucuronic units and 0 to about 5% in iduronic units;
  the sum of the $SO_3^-$ percent in $R_1$, glucuronic units, and in R, iduronic units, is from about 3 to about 7%;
$R_1$ and R being not simultaneously $SO_3^-$ and being both hydrogen in 25-45% of the uronic acid units; the sulfation degree being from about 2.3 to about 2.9, preferably from about 2.4 to about 2.7, and the corresponding cation being a pharmaceutically acceptable one, said mixture of depolymerized chains containing at least 80% of said chains with a molecular weight distribution in the range of from about 2,000 to about 10,000 and a mean molecular weight of from about 4,000 to about 8,000.

Advantageous pharmaceutical compositions comprise, as an active ingredient, a pharmacologically active amount of a glycosaminoglycan constituted by a mixture of chains with a mean molecular weight of from about 6,000 to about 8,000, in which at least 90% of said chains have the formula I above, wherein about 55% of the uronic acid units are those of iduronic acid and $R_3$ is from about 85% to about 90% $SO_3^-$; $R_2$ is about 20% $SO_3^-$; $R_1$ is from about 25% to about 30% $SO_3^-$ in iduronic units and 0 to about 5% $SO_3^-$ in glucuronic units; R is from about 30% to about 35% $SO_3^-$ in glucuronic units and 0 to about 5% in iduronic units; the sum of the $SO_3^-$ percent in $R_1$, glucuronic units and in R, iduronic units, is about 5%; $R_1$ and R being not simultaneously $SO_3^-$ and being both hydrogen in from about 30% to about 40% of the uronic acid units; the sulfation degree being from about 2.5 to about 2.7, the corresponding cation being a chemically or pharmaceutically acceptable one.

A preferred low molecular weight glycosaminoglycan active ingredient of this class is constituted by a mixture of chains with a mean molecular weight of about 7,000, in which at least 90% of said chains have the formula I above, wherein about 55% of the uronic acid units are those of iduronic acid and $R_3$ is about 85% $SO_3^-$;
$R_2$ is about 20% $SO_3^-$;
$R_1$ is about 25% $SO_3^-$ in iduronic units and 0 to about 5% $SO_3^-$ in glucuronic units;
R is about 30% $SO_3^-$ in glucuronic units and 0 to about 5% in iduronic units;
the sum of the $SO_3^-$ percent in $R_1$, glucuronic units, and in R, iduronic units, is about 5%;

$R_1$ and R being not simultaneously $SO_3^-$ and being both hydrogen in about 40% of the uronic acid units; the sulfation degree being about 2.55, the corresponding cation being a pharmaceutically acceptable one. A particular preferred glycosaminoglycan active ingredient has these characteristics, with a mean molecular weight of 7,400.

Finally the present invention refers to the effective amount of said glycosaminoglycans for the control of the coagulation and for an antithrombotic treatment.

Thus, it is a further object of the present invention to provide a method for treating coagulation disorders or for the prevention or treatment of thrombosis in a mammal, which comprises administering to said mammal, in need of said coagulation disorders' treatment or in need of said thrombosis prevention or treatment, a pharmacologically effective amount of a C5-epimerized N,O-sulfate K5 glycosaminoglycan obtainable according to the process wherein steps (i)-(vi) above, including the optional depolymerization and pharmaceutically acceptable salt formation, are performed.

More particularly, said method comprises administering to said mammal a pharmacologically active amount of a glycosaminoglycan constituted by a mixture of chains in which at least 90% of said chains have the formula I as illustrated and specified above.

Preferably, the method of the present invention comprises administering to said mammal a pharmacologically active dose of a pharmaceutical composition as illustrated above.

The following examples illustrate the invention without, however, limiting it.

Example 1

Figure 1:
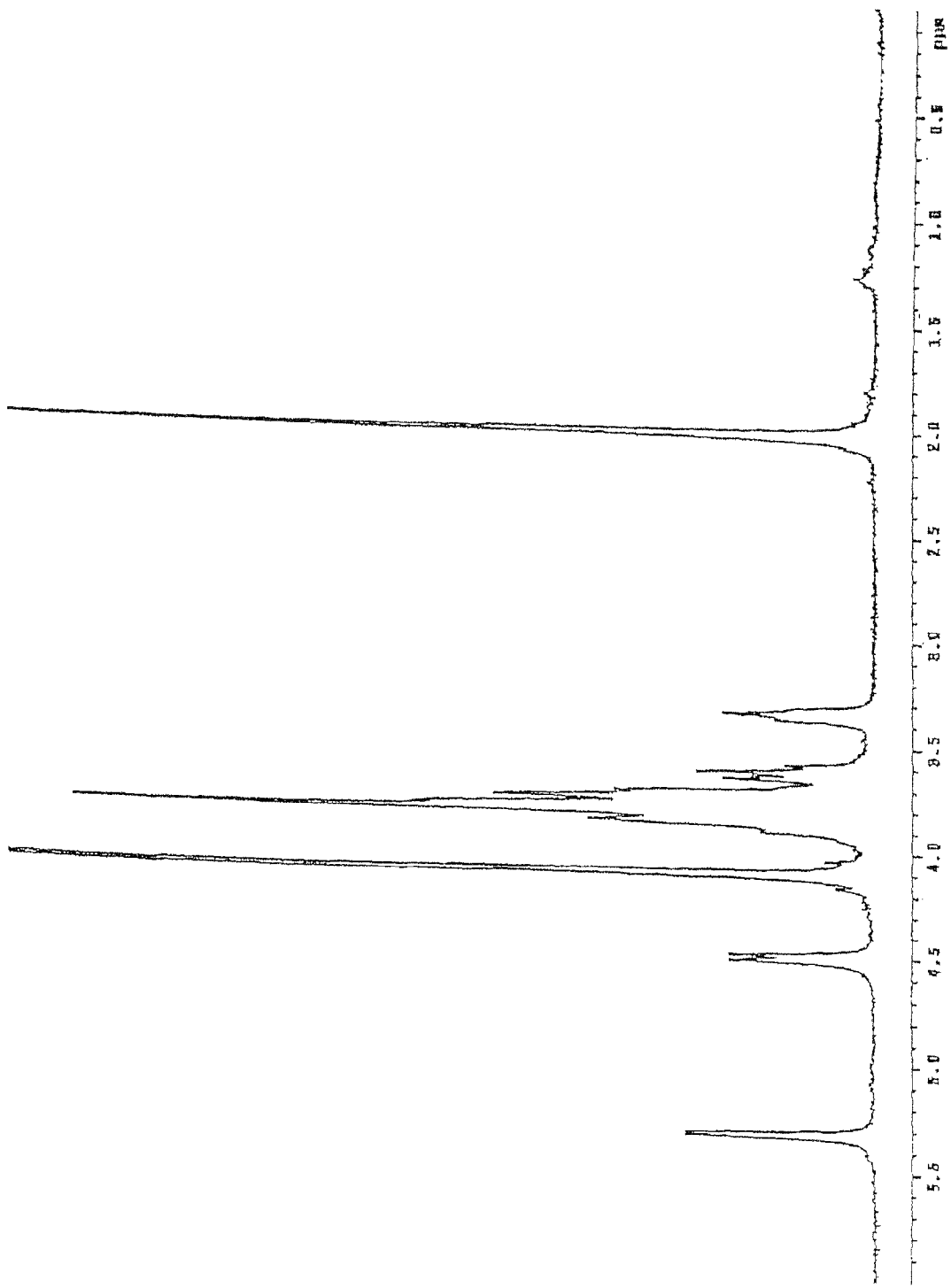
FIG. 1 shows the $^1$H-NMR spectrum of the K5 polysaccharide working standard obtained according to Vann W. F. et al. European Journal of Biochemistry, 1981, 116, 359-364 repeating the purification till the almost complete disappearance of the peaks in the region of 4.9 to 5.2 ppm of the $^1$H-NMR spectrum.
Figure 3:
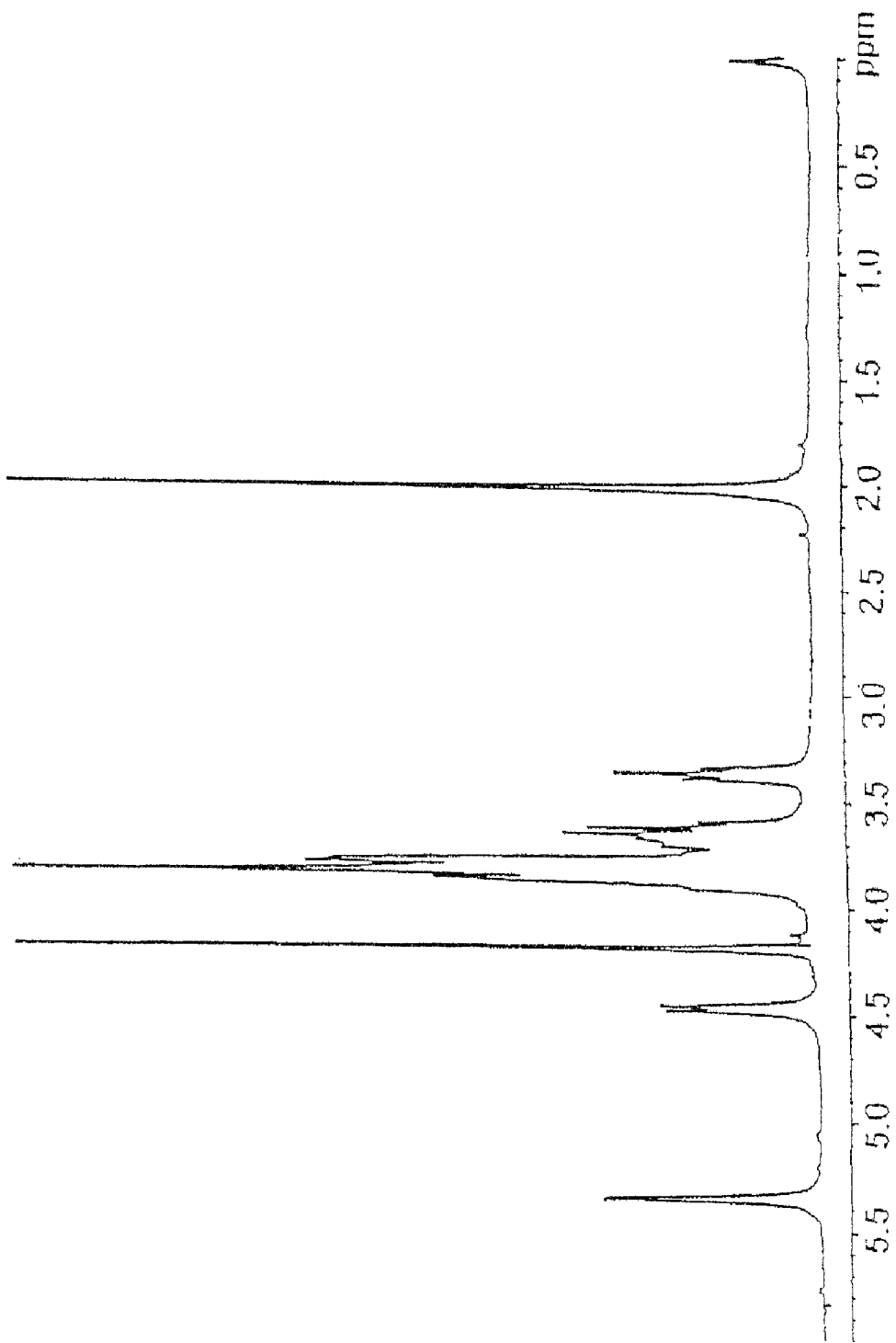
FIG. 3 shows the $^1$H-NMR spectrum of the purified K5 polysaccharide obtained in Example 1 (a) and in Example 12.

Example 1 is performed according to the following steps
(a) 10 g of K5 polysaccharide obtained by fermentation as described in the Italian patent application MI99A001465 (WO 01/02597) with a purity of 80% (FIG. 2) are dissolved in deionized water to obtain a 1% solution. Triton X-100 is added to reach a concentration of 5% and the solution is kept at 55° C. for 2 hours under stilling. The solution is brought to 75° C. and kept at this temperature till a homogeneous turbid system is obtained and then the cooling is rapidly cooled to room temperature. During the cooling two phases are formed. Said thermal treatment is repeated twice on the upper phase (organic phase). The aqueous phase containing K5 is finally 1/10 concentrated under reduced pressure and precipitated with acetone or ethanol. The organic phase is discarded. The product obtained is K5 polysaccharide with 90% purity detected by $^1$H-NMR (FIG. 3) compared to the spectrum of the working standard (FIG. 1).

(b) The product obtained in step (a) is dissolved in 1,000 ml of 2 N sodium hydroxide and kept at 60° C. for 18 hours. The solution is cooled to room temperature and then brought to neutral pH with 6N hydrochloric acid. N-deacetylated K5 is obtained. The solution containing the N-deacetylate K5 is kept at 40° C. and added with 10 g sodium carbonate in one step and 10 g of adduct pyridine.$SO_3$ in 10 minutes. At the end of the reaction the solution is cooled to room temperature and then brought to pH 7.5-8 with a 5% hydrochloric acid solution.

Figure 4:
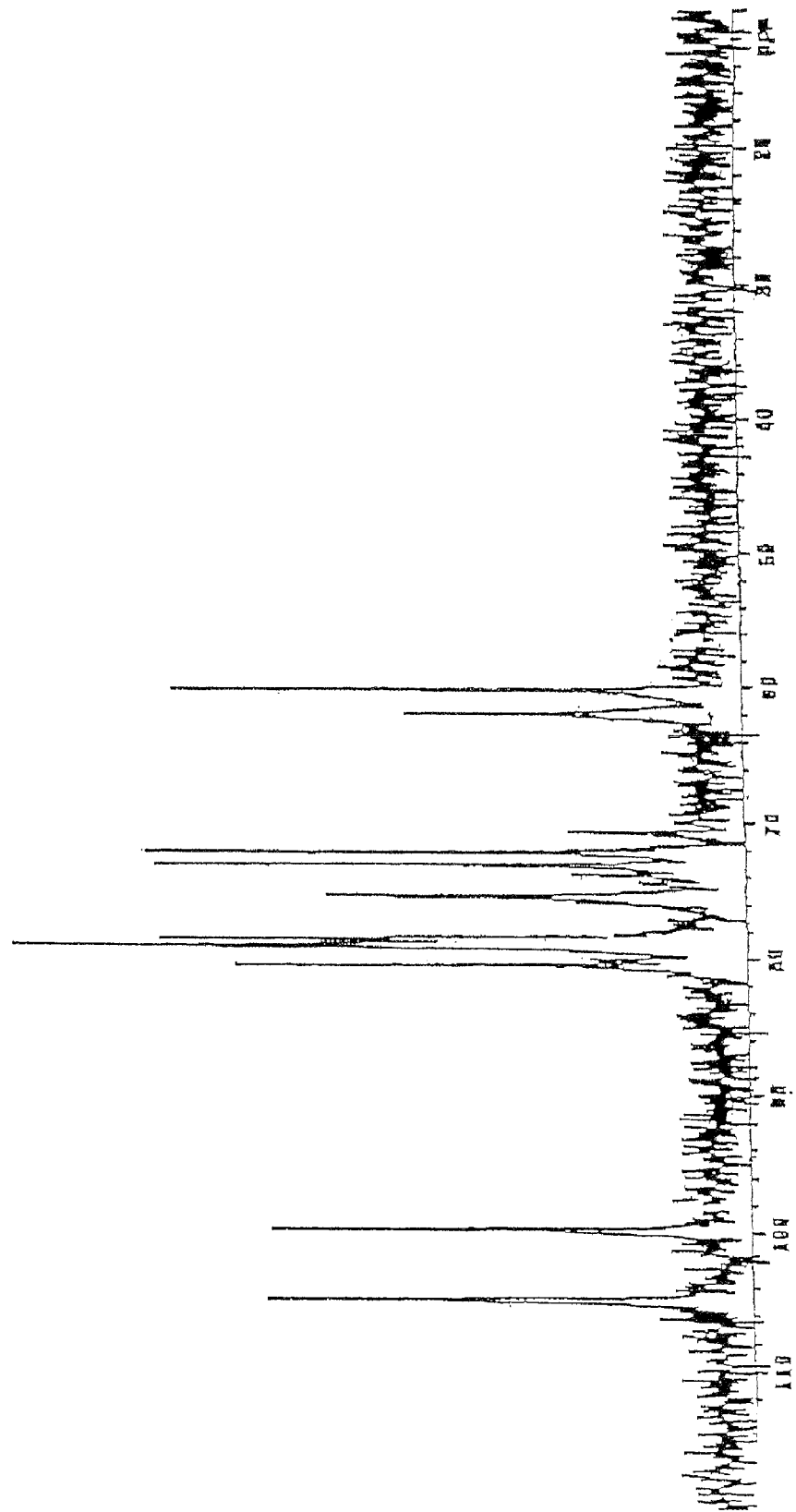
FIG. 4 shows the $^{13}$C-NMR spectrum of the N-sulphate K5 polysaccharide obtained in Example 1(b) and Example 12 (i).

The product obtained, N-sulfated K5, is purified from salts by diafiltration using a 1,000 D cut off spiral membrane (prepscale cartridge—Millipore). The purification process is stopped when the conductivity of the permeate is less than 100 μS. The product retained by the membrane is concentrated to 10% polysaccharide using the same diafiltration system and then is freeze dried. The ratio N-sulfate/N-acetyl in the product obtained is 9.5/0.5 measured by $^{13}$C-NMR (FIG. 4).

(c) 1—Preparation of the Immobilized C5 Epimerase.

Figure 5:
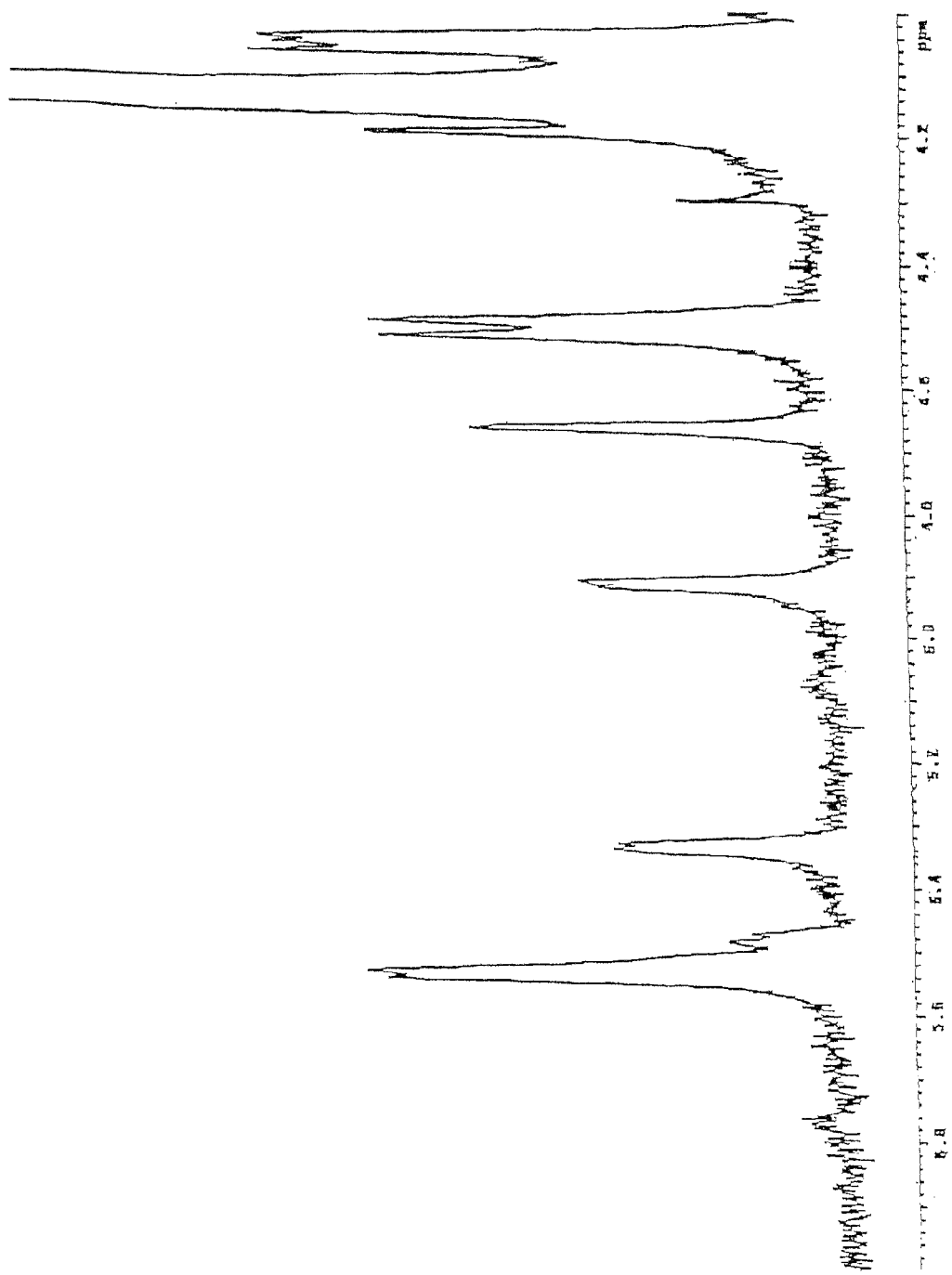
FIG. 5 shows the $^1$H-NMR spectrum of the efficiency of the immobilized C-5 epimerase in Example 1 (c-1) and Example 12 (ii-1).

To 5 mg of recombinant C5 epimerase obtained according to WO98/48006 corresponding to $1.2 \times 10^{11}$ cpm (counts per minutes) dissolved in 200 ml of 25 mM Hepes buffer pH 7.4, containing 0.1 M KCl, 0.1% Triton X-100 and 15 mM EDTA, 100 mg of N-sulfated K5 obtained as described in step (b) are added. The solution is diafiltrated with a 30,000 D membrane at 4° C. till disappearance of N-sulfate K5 in the permeate. To the solution rententated by the membrane the buffer is changed by diafiltration against 200 mM $NaHCO_3$ at pH 7 and, after concentration to 50 ml, 50 ml of CNBr activated Sepharose 4B resin are added and kept to react overnight at 4° C. At the end of the reaction the amount of residual enzyme in the supernatant is measured with the Quantigold method (Diversified Biotec) after centrifugation. The enzyme in the supernatant is absent, showing that with the method described the enzyme is 100% immobilized. To occupy the sites still available, the resin is washed with 100 mM tris pH 8. To measure the activity of the immobilized enzyme an amount of immobilized enzyme theoretically corresponding to $1.2 \times 10^7$ cpm is loaded into a column. In the column obtained 1 mg of N-sulfated K5 obtained as described in step (b) dissolved in 25 mM Hepes, 0.1M KCl, 0.015 M EDTA, 0.01% Triton X-100, pH 7.4 buffer is dissolved, recirculating it through said column at 37° C. overnight at a flow rate of 0.5 ml/minute. After purification by DEAE chromatographic system and desalting on a Sephadex G-10 the sample is freeze dried and analyzed for its content in iduronic acid by $^1$H-NMR as described in WO 96/14425. The ratio iduronic acid/glucuronic acid is 30/70 (FIG. 5).

2—Epimerization.

An amount of 10 g of N-sulfate K5 is dissolved in 600 ml of 25 mM Hepes buffer pH 6.5 containing 50 mM $CaCl_2$. The solution obtained is recirculated through a column of 50 ml containing the resin with the immobilized enzyme. This reaction is performed at 37° C. with a flow rate of 200 ml/hour for 24 hours. The product obtained is purified by ultrafiltration and precipitation with ethanol. The pellet is dissolved in water at 10% concentration.

Figure 6:
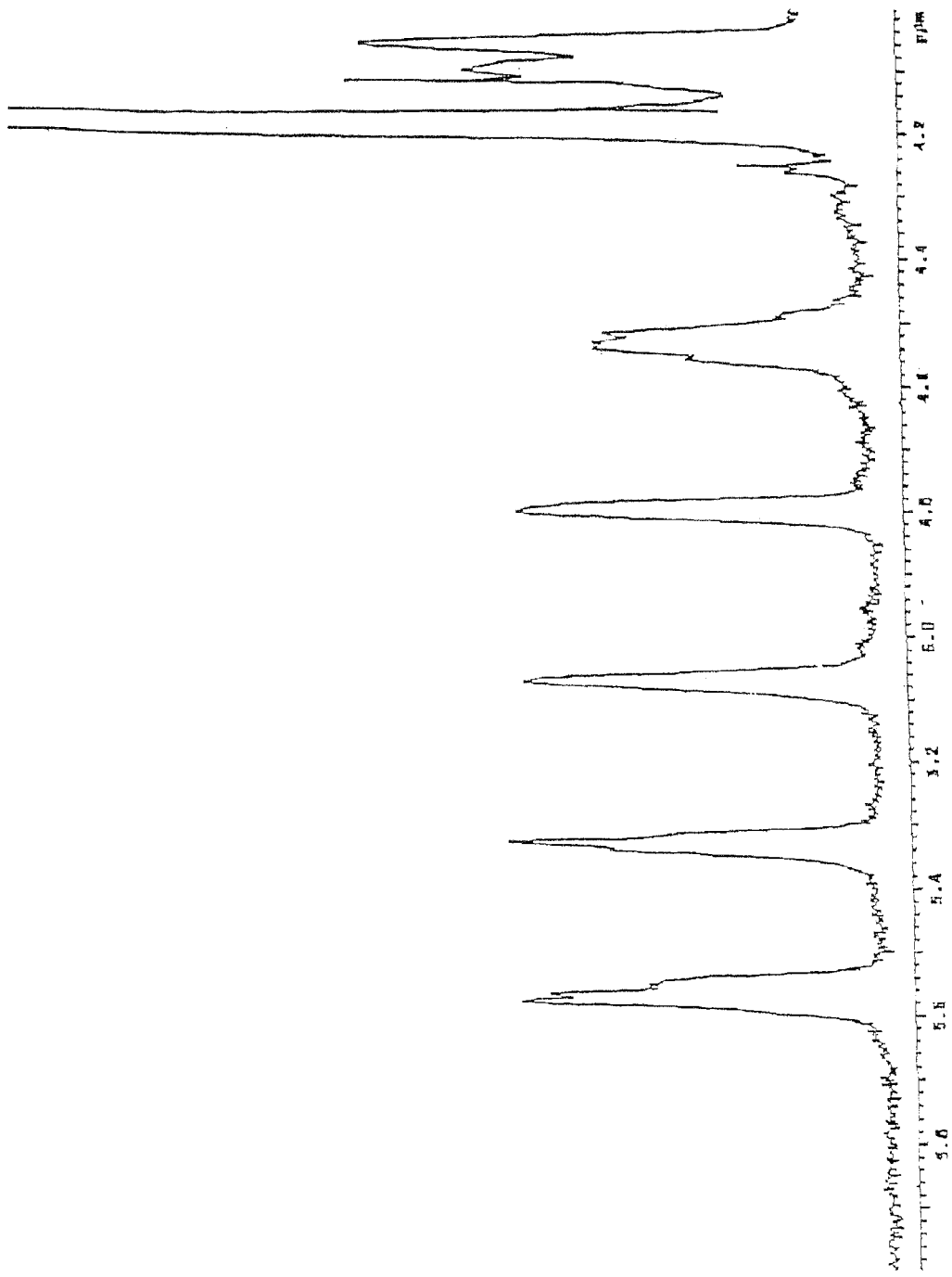
FIG. 6 shows the $^1$H-NMR spectrum of the epimerized product obtained in Example 1 (c-2).

An epimerized product is obtained with an iduronic acid/glucuronic acid ratio of 48/52 against a ratio 0/100 of the starting material. The percentage of epimerization is calculated by $^1$H-NMR (FIG. 6). The yield calculated measuring the uronic acid content against standard by the carbazole method (Bitter and Muir Anal. Biochem., 1971, 39 88-92) is 90%.

(d) The solution containing the epimerized product with 10% concentration obtained in step (c) is cooled to 10° C. with a cooling bath and then applied onto a IR 120 H$^+$ cationic exchange resin (50 ml). Both the column and the container of the eluted solution are kept at 10° C. After the passage of the solution the resin is washed with 3 volumes of deionized water. The pH of the flow through is more than 6. The acidic solution is brought to neutrality with an aqueous solution of 15% tetrabutylammoniun hydroxide. The solution is concentrated to 1/10 of the volume in a rotating evaporator under vacuum and freeze dried. The product is suspended in 200 ml of DMF and added with 150 g of the adduct pyridine.SO$_3$ dissolved in 200 ml of DMF. The solution is kept at 45° C. for 18 hours. At the end of the reaction the solution is cooled to room temperature and added with 1,200 ml of acetone saturated with sodium chloride. The pellet obtained is separated from the solvent by filtration, dissolved with 100 ml of deionized water and sodium chloride is added to 0.2 M concentration. The solution is brought to pH 7.5-8 with 2N sodium hydroxide and 300 ml of acetone are added. The pellet is separated by filtration. The solid obtained is solubilized with 100 ml deionized water and purified from the residual salts by diafiltration as described in step (b). The $^{13}$C-NMR analysis on a dried small amount of the oversulfated product is shown in FIG. 7.

Figure 8:
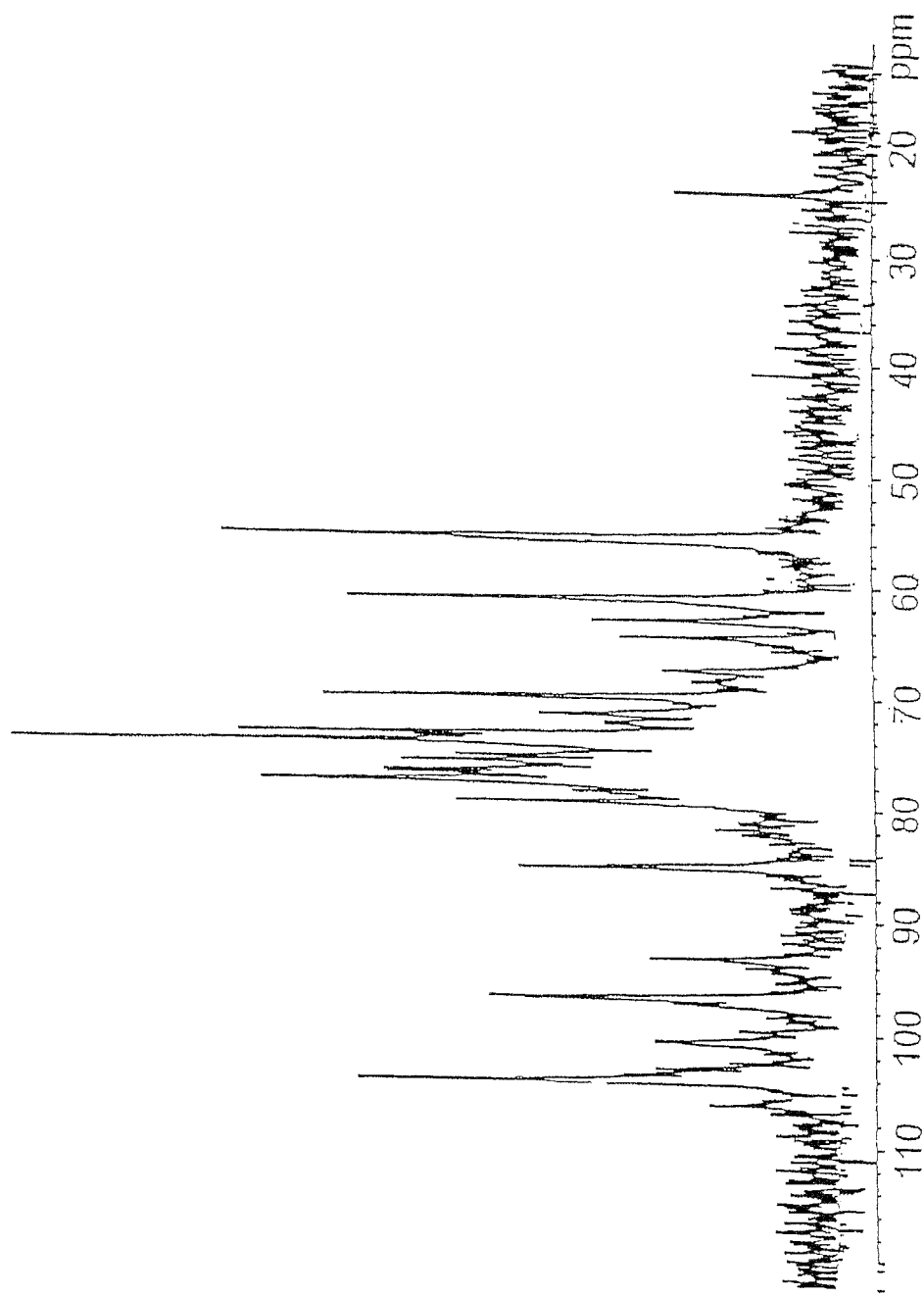
FIG. 8 shows the $^{13}$C-NMR spectrum of the desulfated compound obtained in Example 1 (e).

(e) The solution containing the product of step (d) is passed onto a IR 120 H$^+$ cationic exchange resin (50 ml). After the passage of the solution the resin is washed with 3 volumes of deionized water. The pH of the flow through is more than 6. The acidic solution is brought to neutrality with pyridine. The solution is concentrated to 1/10 of the volume in a rotating evaporator at 40° C. under vacuum and freeze dried. The product obtained as pyridine salt is added with 500 ml of a solution of DMSO/methanol (9/1 V/V). The solution is kept at 60° C. for 3.5 hours and then added with 50 ml deionized water and finally treated with 1,650 ml acetone saturated with sodium chloride. The solid obtained is purified by diafiltration as described in step (b) and a solution at 10% concentration is obtained. The $^{13}$C-NMR analysis on a dried small amount in FIG. 8 shows a content of sulfate groups in position 6 of the amino sugar of 35%.

(f) The solution containing the product of step (e) is passed onto a IR 120 H$^+$ cationic exchange resin (50 ml). After the passage of the solution the resin is washed with 3 volumes of deionized water. The pH of the flow through is more than 6. The acidic solution is brought to neutrality with an aqueous solution of 15% tetrabutylammoniun hydroxide. The solution is concentrated to 1/10 of the volume in a rotating evaporator under vacuum and freeze dried. The product as tetrabutylammonium salt is suspended in 200 ml DMF. The suspension is cooled to 0° C. and treated with 40 g of the adduct pyridine.SO$_3$ dissolved in 100 ml DMF. The sulfating agent is added one step. The solution is kept at 0° C. for 1.5 hours and then is treated with 750 ml acetone saturated with sodium chloride. The solid obtained is purified by diafiltration as described in step (b).

Figure 9:
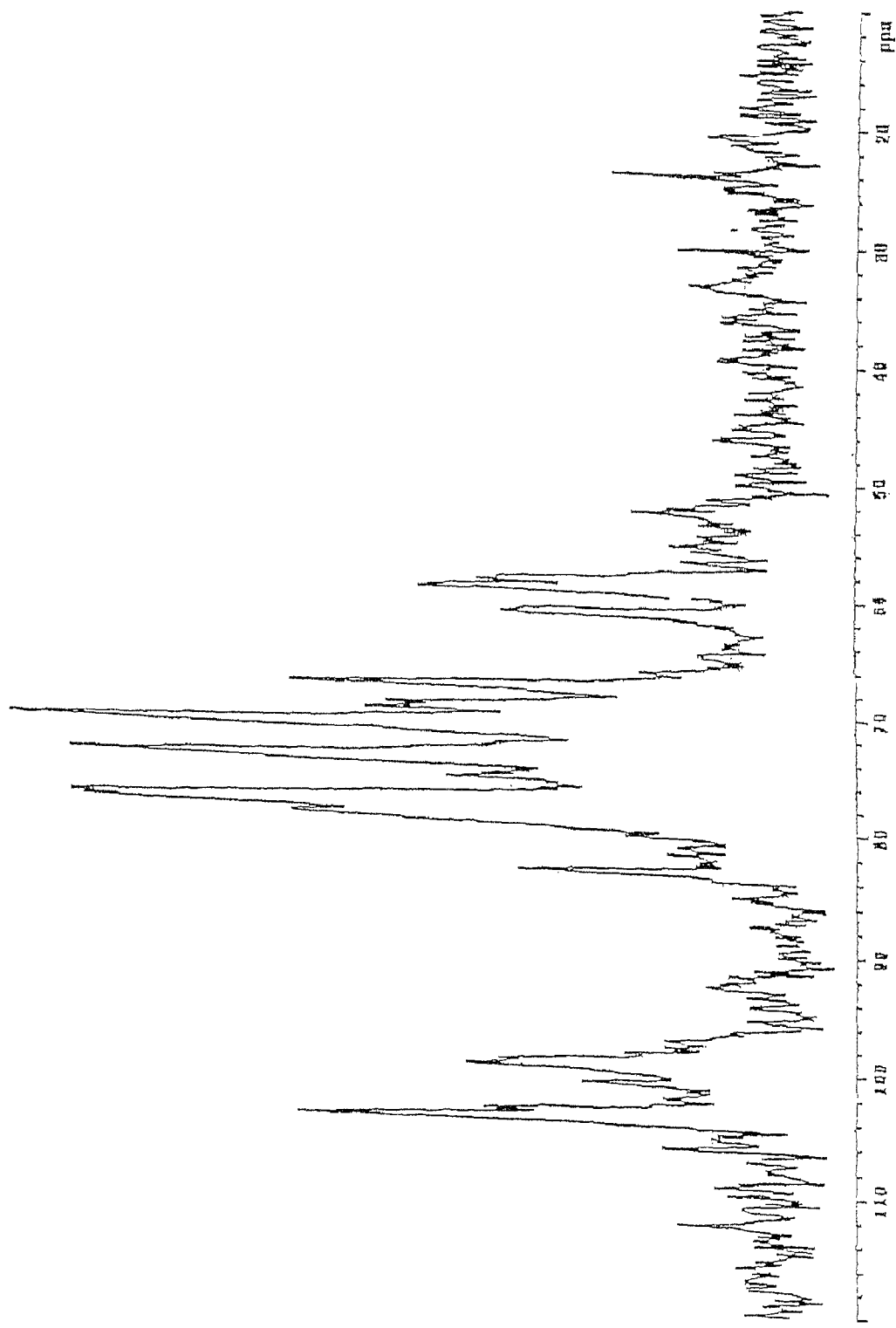
FIG. 9 shows the $^{13}$C-NMR spectrum of the compound obtained in Example 1 (g).

(g) The solution of step (f) is treated as described in step (b) for N-sulfation, i.e. by adding an aqueous solution containing the solid obtained at the end of step (f), at 40° C., with sodium carbonate in one step and of adduct pyridine.SO$_3$ in 10 minutes and isolating the N-deacetylated, N,O-sulfated, C5-epimerized.K5 polysaccharide thus obtained. The $^{13}$C-NMR on a dried small amount of the product obtained is shown in FIG. 9. The product obtained shows the physico-chemical and biological characteristics of Table 2-line 3 compared with the 4th International Standard Heparin and the 1st International Standard Low Molecular Weight Heparin.

Example 2

Example 1 was repeated but in step (c) the immobilized enzyme C5 epimerase extracted from murine mastocytoma was used as described by Jacobsson et al., J. Biol. Chem., 1979, 254, 2975-2982, in a buffer containing 40 mM CaCl$_2$ pH 7.4. The product obtained has a ratio iduronic acid/glucuronic acid of 59.5:40.5 and the characteristics described in Table 2, line 4.

Example 3

Example 1 was repeated but in step (c) the immobilized enzyme C5 epimerase extracted from bovine liver was used as described in WO96/14425 with a reaction buffer at pH 7.4 and reaction time of 32 hours. Moreover in step (e) the reaction time was 4 hours. The product obtained has a ratio iduronic acid/glucuronic acid of 55.4:44.6 and the characteristics described in Table 2, line 5.

Example 4

Example 1 was repeated but in step (c) the recombinant enzyme C5 epimerase in solution was used using for the epimerization 10 g N-sulfate K5 dissolved in 1,000 ml of 25 mM Hepes buffer pH 6.5 containing 50 mM CaCl$_2$. To this solution $1.5 \times 10^{11}$ cpm equivalents of recombinant enzyme described in Example 1 are added. The solution is kept at 37° C. for 24 hours. The solution is then treated at 100° C. for 10 minutes to denature the enzyme and finally is filtered on a 0.45µ filter to obtain a clear solution containing the product. The product obtained is then purified by diafiltration and precipitation with ethanol or acetone. The pellet is dissolved in water at 10% concentration and treated like in Example 1 keeping the reaction time of step (e) for 2 hours.

The product obtained has a ratio iduronic acid/glucuronic acid of 56:44 and the characteristics described in Table 2, line 6.

Example 5

Example 4 is repeated using in step (c) the enzyme from murine mastocytoma described in Example 2, in solution, with the reaction buffer at pH 7.4 containing 40 mM BaCl$_2$ and performing the reaction for 18 hours. Moreover in step (e) the reaction time is 3 hours. The product obtained has a ratio iduronic acid/glucuronic acid of 40.1:59.9 and the characteristics described in Table 2, line 7.

Example 6

Example 4 is repeated using in step (c) the enzyme from bovine liver of Example 3, in solution, with the reaction buffer containing 12.5 mM MnCl$_2$ and performing the reaction for 14 hours. Moreover in step (e) the reaction time is 4 hours. The product obtained has a ratio iduronic acid/glucuronic acid of 44.3:55.7 and the characteristics described in Table 2, line 8.

Example 7

Example 4 is repeated using in step (c) a reaction buffer at pH 7.4 containing 37.5 mM $MgCl_2$ and performing the reaction for 16 hours. Moreover in step (e) the reaction time is 4 hours. The product obtained has a ratio iduronic acid/glucuronic acid of 47.5:52.5 and the characteristics described in Table 2, line 9.

Example 8

Example 3 is repeated using in step (c) a reaction buffer at pH 7.0 containing 10 mM $MgCl_2$, 5 mM $CaCl_2$, 10 mM $MnCl_2$ and performing the reaction for 24 hours. Moreover in step (e) the reaction time is 3 hours. The product obtained has a ratio iduronic acid/glucuronic acid of 44.8:55.2 and the characteristics described in Table 2, line 10.

Example 9

Example 6 is repeated using in step (c) a reaction buffer at pH 7.4 containing 10 mM $MgCl_2$, 5 mM $CaCl_2$, 10 mM $MnCl_2$ and performing the reaction for 24 hours. Moreover in step (e) the reaction time is 3 hours. The product obtained has a ratio iduronic acid/glucuronic acid of 52:48 and the characteristics described in Table 2, line 11.

Example 10

Figure 10:
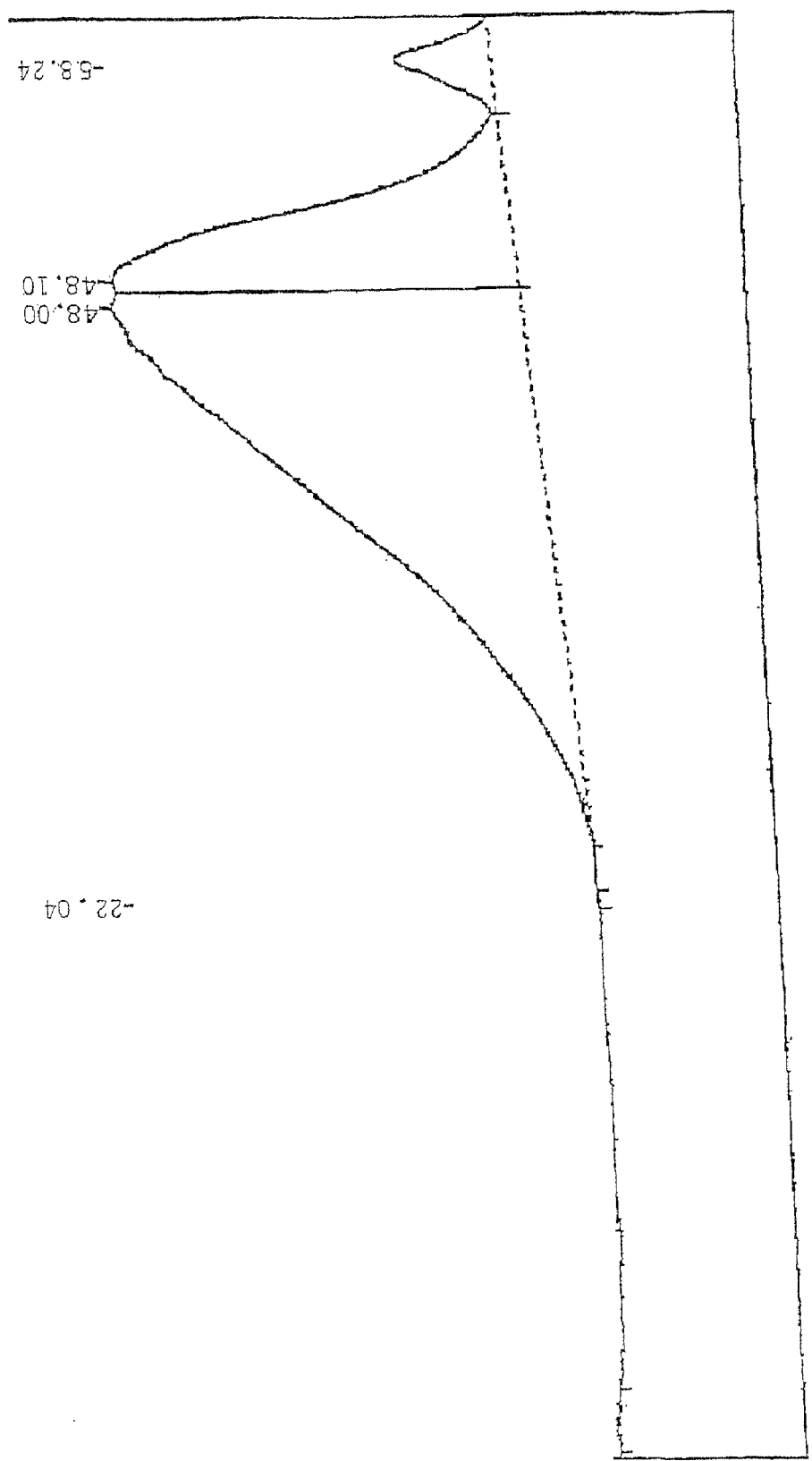
FIG. 10 shows the chromatographic profile of the compound obtained in Example 3.
Figure 11A:
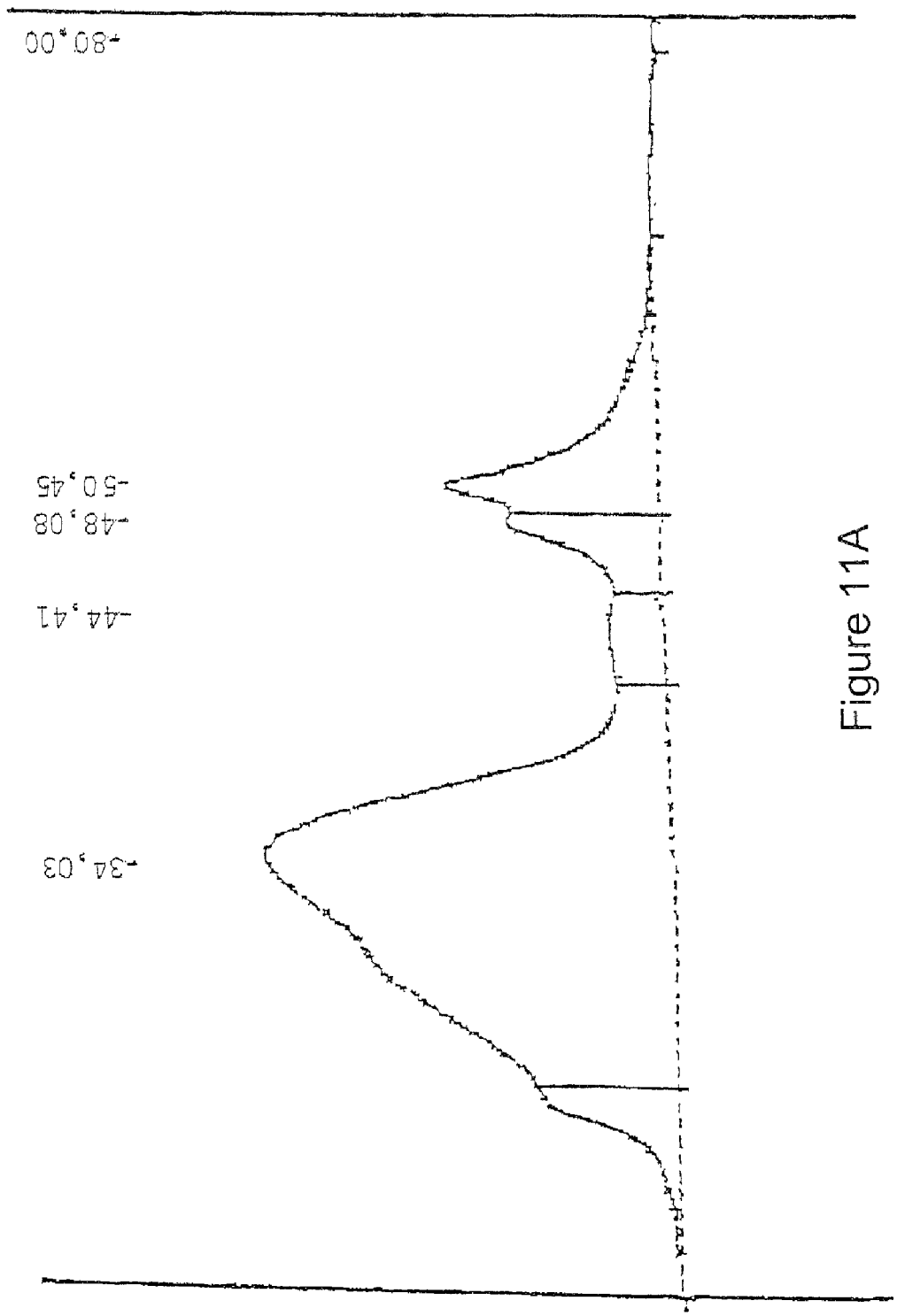
FIG. 11A shows the chromatographic profile of the compound at high molecular weight obtained in Example 10.
Figure 11B:
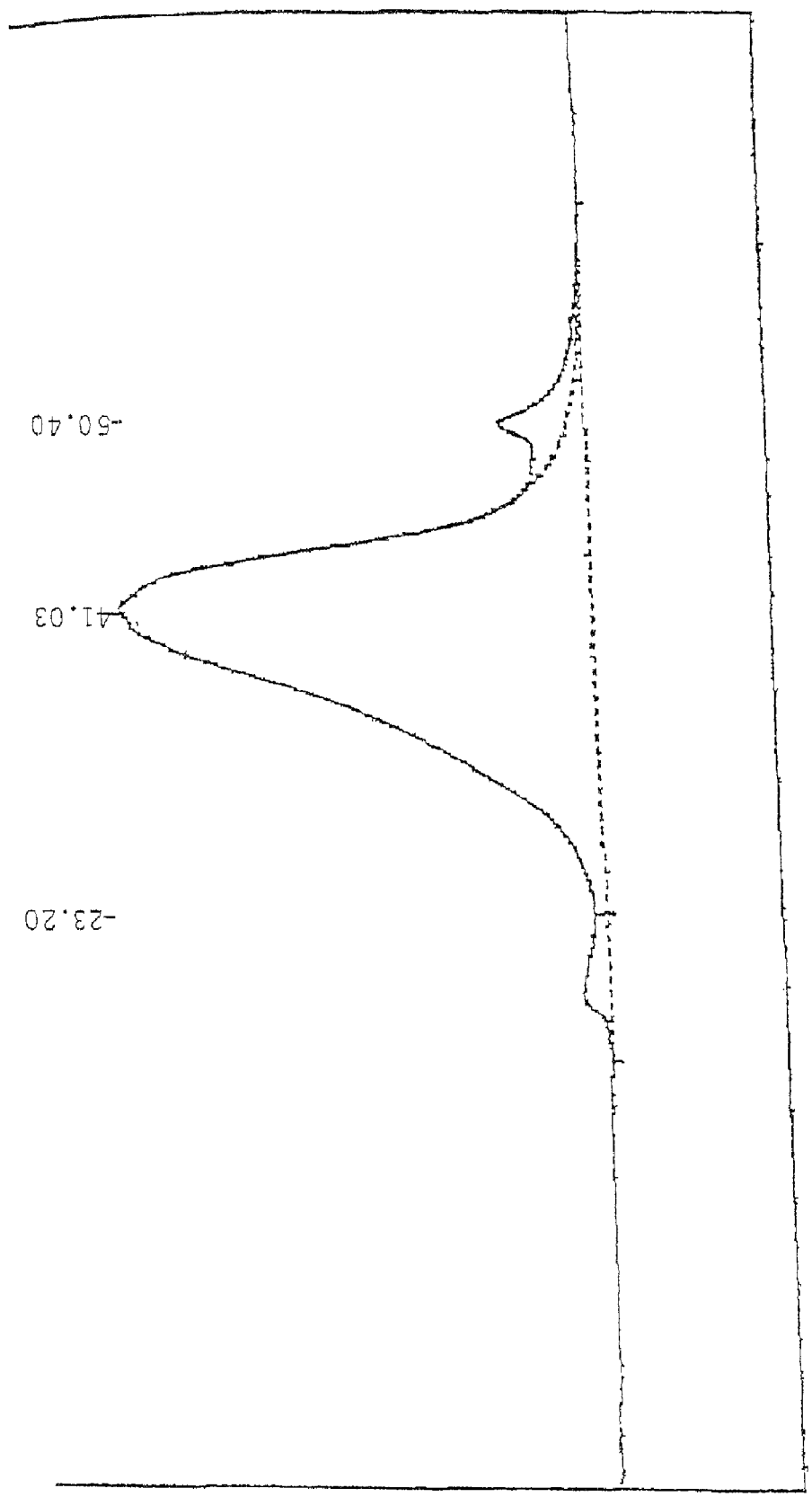
FIG. 11B shows the chromatographic profile of the compound at low molecular weight obtained in Example 10.

The sample obtained in Example 3 having a molecular weight distribution calculated according to Harenberg and De Vries in J. Chromatography, 1983, 261, 287-292 (FIG. 10) is fractionated by gel filtration. In particular 1 g of product is dissolved in 20 ml of 1M NaCl solution and loaded onto a column containing 1,000 ml of Sephacryl HR S-400 resin (Amersham-Pharmacia). The column is then eluted with 2,000 ml of 1M NaCl solution and collected in 50 ml fractions by fraction collector (Gilson). After the determination of product content on each fraction by carbazole reaction (Bitter and Muir, 1971) the fractions containing the sample are combined in fraction A and fraction B respectively corresponding to the high molecular weight and low molecular weight fraction. These fractions are concentrated at 10% of the volume by evaporator under vacuum and are desalted on a column containing 500 ml of Sephadex G-10 resin (Amersham-Pharmacia). The solutions containing the desalted products are freeze dried obtaining fraction A and fraction B (FIG. 11A and FIG. 11B). The products obtained show the characteristics described in Table 2, lines 12 and 13.

Example 11

The sample obtained in Example 4 is degraded with nitrous acid in a controlled way as described in WO 82/03627. In particular, 5 g of sample are dissolved in 250 ml of water and cooled to 4° C. with a thermostatic bath. The pH is brought to 2 with 1N hydrochloric acid cooled at 4° C. and then 10 ml of a solution of 1% sodium nitrite are added. If necessary the pH is brought to 2 with 1N hydrochloric acid and is kept under slow stirring for 15 minutes. The solution is neutralized with 1N NaOH cooled at 4° C. Then 250 mg of sodium borohydride dissolved in 13 ml of deionized water are added and the reaction is maintained for 4 hours. The pH is brought to 5 with 1N hydrochloric acid and the reaction kept for 10 minutes to destroy the excess of sodium borohydride, and then neutralized with 1N NaOH. The product is recovered by precipitation with 3 volumes of ethanol and then dried in a vacuum oven. The product obtained shows the characteristics described in Table 2, line 14.

TABLE 2

Anticoagulant and antithrombotic activity of the products obtained in the described examples.

| | 1) Anti Xa (%) | 2) aPTT (%) | 3) HCII (%) | 4) Anti IIa (%) | 5) MW | 6) Affinity ATIII (%) |
|---|---|---|---|---|---|---|
| Unfractionated Hep (4$^{th}$ int. STD) | 100 | 100 | 100 | 100 | 13,500 | 32% |
| LMW heparin (1$^{st}$ Int. Std) | 84 | 30 | | 33 | 4,500 | n.d. |
| Example 1 | 76.6 | 43.4 | 256 | 118 | 15,200 | 29 |
| Example 2 | 94.3 | 57 | 294 | 208 | 13,500 | 29.5 |
| Example 3 | 112 | 88 | 346 | 223 | 14,600 | 28 |
| Example 4 | 157 | 71.5 | 362 | 600 | 22,500 a) 13,000 b) | 29 |
| Example 5 | 150 | 70 | 352 | 213 | 24,000 a) 13,100 b) | 31 |
| Example 6 | 150 | 79 | 335 | 333 | 23,000 a) 12,600 b) | 33 |
| Example 7 | 120 | 92 | 346 | 247 | 13,000 a) 10,100 b) | 29 |
| Example 8 | 153 | 75 | 332 | 240 | 22,500 a) 13,000 b) | 34 |
| Example 9 | 157 | 71 | 346 | 233 | 23,000 a) 12,600 b) | 35 |
| Example 10-A | 250 | 70.8 | 480 | 435 | 30,000 | 48 |
| Example 10-B | 43 | 77.7 | 145 | 27.3 | 7,600 | 24 |
| Example 11 | 97.5 | 55.5 | 230 | 210 | 5,400 | 25 |

The references from 1) to 6) have the same meaning as for Table 1.

From the table it is evident that the product obtained by the present process shows activities comparable to the extractive heparin in the Anti-Xa test (1) while the global anticoagulant activity is reduced (2) and the tests which refer to thrombin inhibition are markedly higher (3,4). These characteristics of the product result in higher antithrombotic properties and lower side effects such as bleeding effect if compared to the extractive heparin.

Example 12

Example 12 is performed starting from 10 g of polysaccharide obtained by fermentation as described in the Italian application MI99A001465 (WO 01/02597) with a purity of 80% (FIG. 2) which are dissolved in deionized water to obtain a 1% solution. Triton X-100 is added to reach a concentration of 5% and the solution is kept at 55° C. for 2 hours under stirring. The solution is brought to 75° C. and kept at this temperature till a homogeneous turbid system is obtained and then the solution is rapidly cooled to room temperature. During the cooling two phases are formed. Said thermal treatment is repeated twice on the upper phase (organic phase). The aqueous phase containing K5 is finally 1/10 concentrated under reduced pressure and precipitated with acetone or ethanol. The organic phase is discarded.

The product obtained is K5 with 90% purity detected by $^1$H-NMR (FIG. 3) compared to the spectrum of the working standard (FIG. 1) and a retention time of 9 minutes on the HPLC analysis using two columns (Bio Rad Bio-sil SEC 250).

The process proceeds according to the following steps:
(i) The thus purified K5 is dissolved in 1,000 ml of 2 N sodium hydroxide and kept at 60° C. for 18 hours. The solution is cooled to room temperature and then brought to neutral pH with 6N hydrochloric acid. N-deacetylated K5 is obtained.

The solution containing the N-deacetylated K5 is kept at 40° C. and added with 10 gr sodium carbonate in one step and 20 g of adduct pyridine.$SO_3$ in 10 minutes. At the end of the reaction the solution is cooled to room temperature and then brought to pH 7.5-8 with a 5% hydrochloric acid solution.

The product obtained, N-sulfate-K5, is purified from salts by diafiltration using a 1,000 D cut off spiral membrane (prepscale cartridge—Millipore). The purification process is stopped when the conductivity of the permeate is less than 100 µS. The product retained by the membrane is concentrated to 10% polysaccharide using the same diafiltration system and then is freeze dried.

The ratio N-sulfate/N-acetyl in the product obtained is 9.5/0.5 measured by $^{13}$C-NMR (FIG. 4).
(ii) 1—Preparation of the immobilized C5 epimerase
To 5 mg of recombinant C5 epimerase obtained according to WO 98/48006, corresponding to $1.2 \times 10^{11}$ cpm (counts per minutes) dissolved in 200 ml of 25 mM Hepes buffer pH 7.4, containing 0.1 M KCl, 0.1% Triton X-100 and 0.015 M ethylenediaminotetracetic acid (EDTA), 100 mg of N-sulfate K5 obtained as described in step (i) are added. The solution is diafiltrated with a 30,000 D membrane at 4° C. till disappearance of N-sulfate K5 in the permeate. To the solution rentenated by the membrane the buffer is changed by diafiltration against 200 mM NaHCO$_3$ at pH 7 and, after concentration to 50 ml, 50 ml of CNBr activated Sepharose 4B resin are added and kept to react overnight at 4° C. At the end of the reaction the amount of residual enzyme in the supernatant is measured with the Quantigold method (Diversified Biotec) after centrifugation. The enzyme in the supernatant is absent, showing that with the method described the enzyme is 100% immobilized. To occupy the sites still available the resin is washed with 100 mM tris pH 8. To measure the activity of the immobilized enzyme an amount of immobilized enzyme theoretically correspondent to $1.2 \times 10^7$ cpm is loaded into a column. In the column obtained 1 mg of N-sulfate K5 obtained as described in step (b) dissolved in 25 mM Hepes, 0.1M KCl, 0.015 M EDTA, 0.01% Triton X-100, pH 7.4 buffer is dissolved, recirculating it through said column at 37° C. overnight at a flow rate of 0.5 ml/minute.

After purification by DEAE chromatographic system and desalting on a Sephadex G-10 the sample is freeze dried and analyzed for its content in iduronic acid by $^1$H-NMR technique as already described in WO 96/14425. The ratio iduronic acid/glucuronic acid is 30/70 (FIG. 5).
2—Epimerization.
An amount of 10 g of the N-sulfate K5 is dissolved in 600 ml of 25 mM Hepes buffer pH 7 containing 50 mM CaCl$_2$. The solution obtained is recirculated through a column of 50 ml containing the resin with the immobilized enzyme.

This reaction is performed at 30° C. with a flow rate of 200 ml/hour for 24 hours. The product obtained is purified by ultrafiltration and precipitation with ethanol. The pellet is dissolved in water at 10% concentration.

Figure 12:
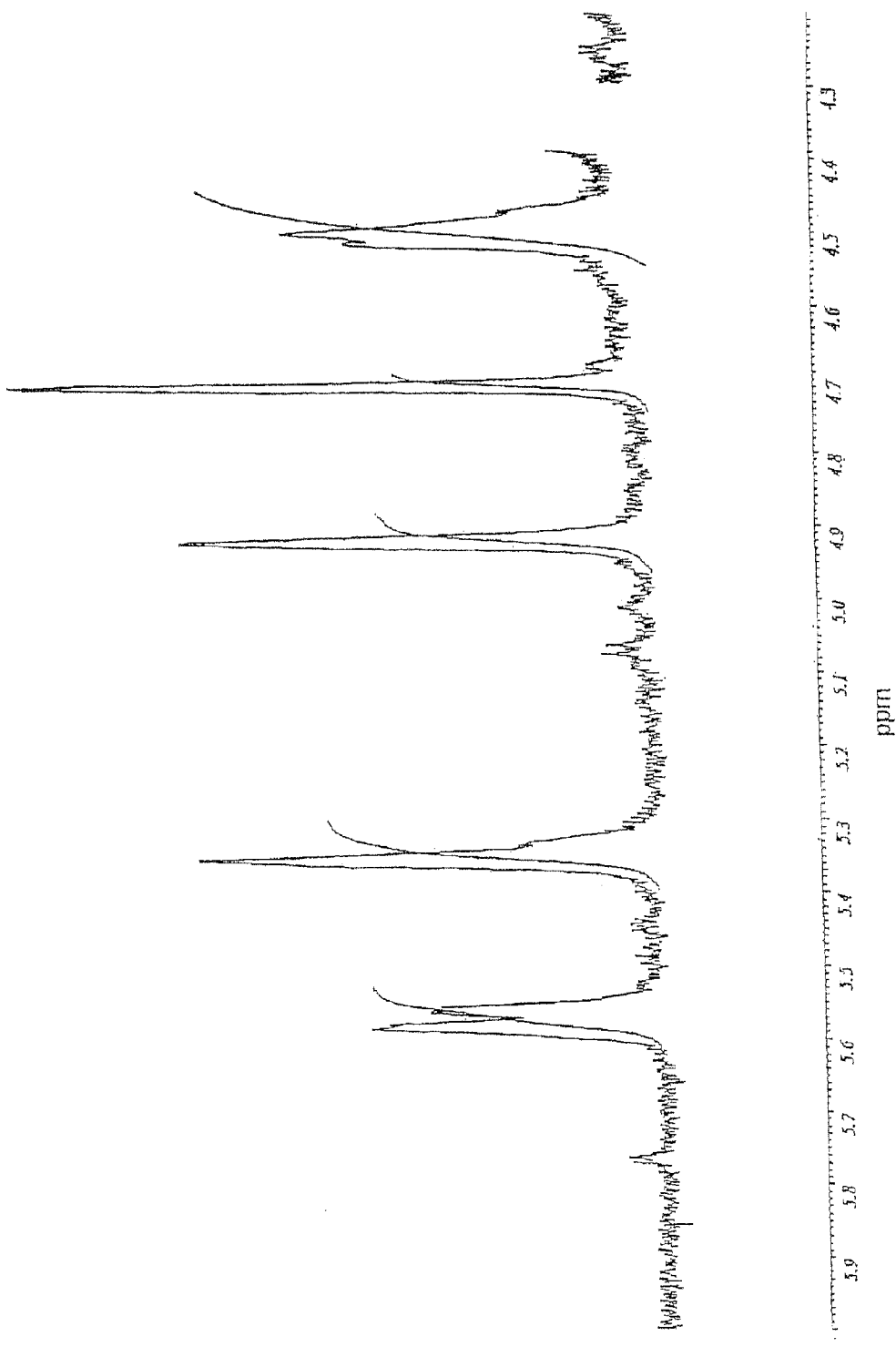
FIG. 12 shows the $^1$H-NMR spectrum of the epimerized product obtained in Example 12 (ii)
Figure 13:
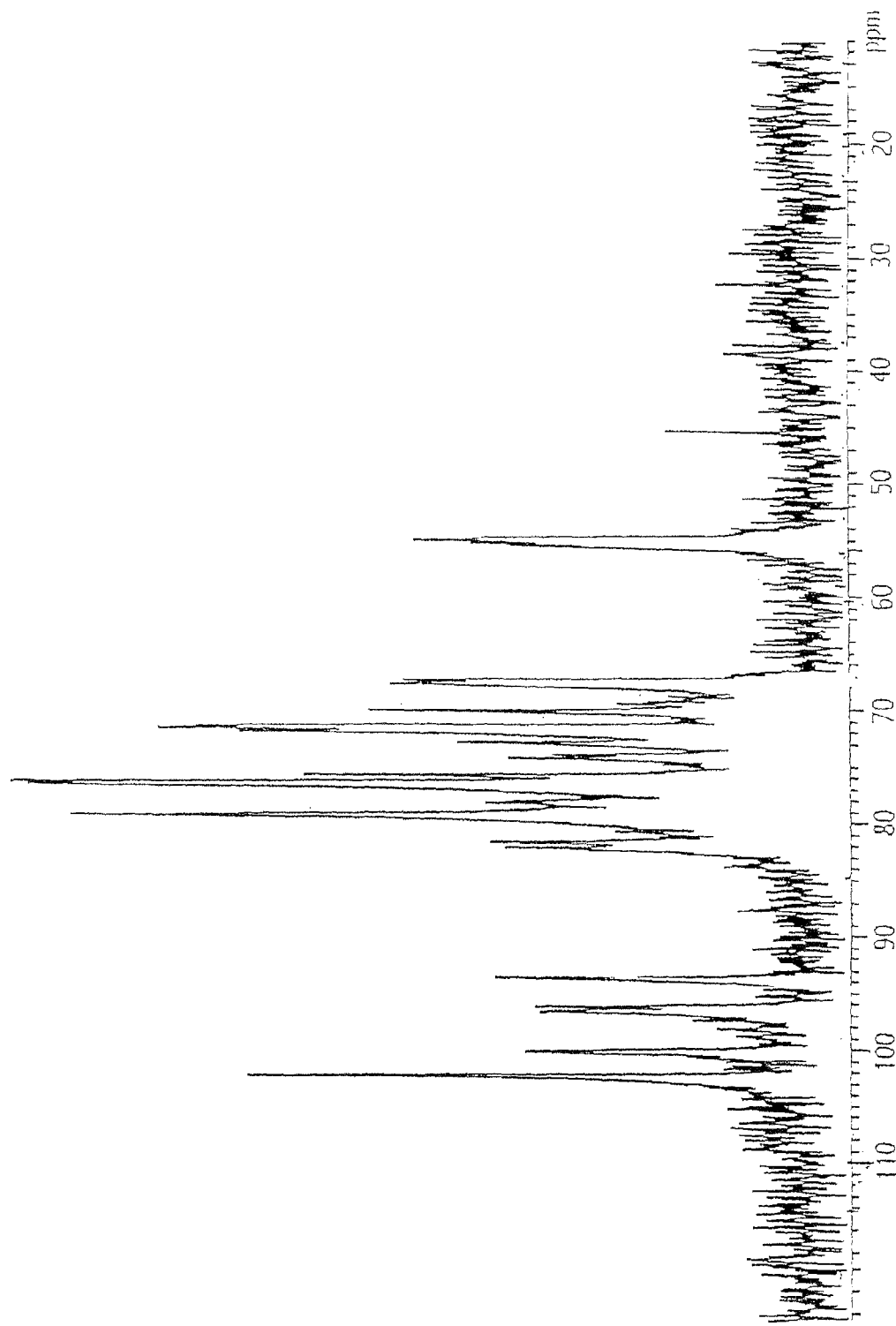
FIG. 13 shows the $^{13}$C-NMR spectrum of the oversulfated compound obtained in Example 12 (iii).
Figure 14:
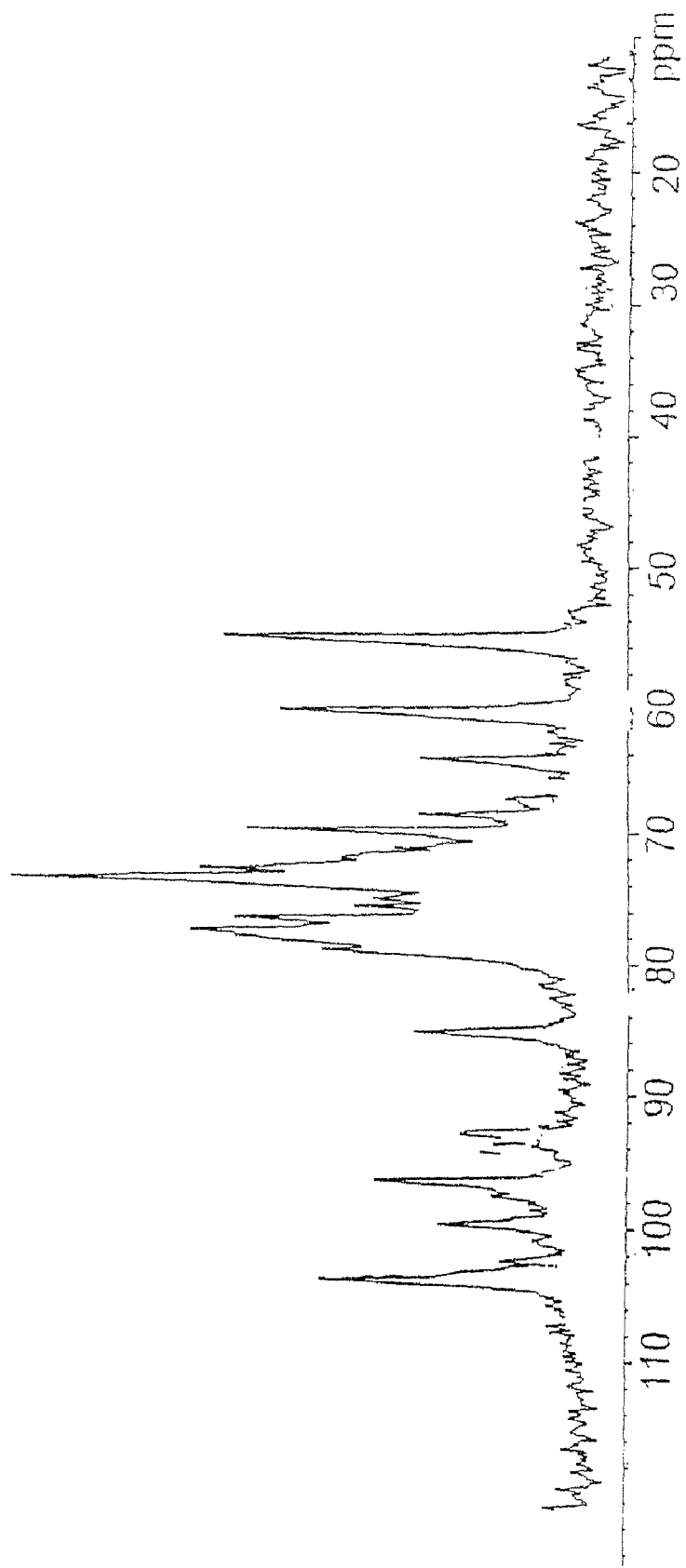
FIG. 14 shows the $^{13}$C-NMR spectrum of the desulfated compound obtained in Example 12 (iv).

An epimerized product is obtained with a ratio iduronic acid/glucuronic acid 54/46 against a ratio 0/100 of the starting material. The percentage of epimerization is calculated by $^1$H-NMR (FIG. 12). The yield calculated measuring the uronic acid content against standard by the carbazole method (Bitter and Muir, 1971) is 90%.
(iii) The solution containing the epimerized product obtained in step (ii) is cooled to 10° C. with a cooling bath and then applied onto a IR 120 H$^+$ cationic exchange resin (50 ml). Both the column and the container of the eluted solution are kept at 10° C. After the passage of the solution the resin is washed with 3 volumes of deionized water. The pH of the flow through is more than 6. The acidic solution is brought to neutrality with a 15% aqueous solution of tetrabutylammoniun hydroxide. The solution is concentrated to 1/10 of the volume in a rotating evaporator under vacuum and freeze dried. The product is suspended in 200 ml of dimethylformamide (DMF) and added with 150 g of the adduct pyridine.SO$_3$ dissolved in 200 ml of DMF. The solution is kept at 45° C. for 18 hours. At the end of the reaction the solution is cooled to room temperature and added with 1,200 ml of acetone saturated with sodium chloride. The pellet obtained is separated from the solvent by filtration, dissolved with 100 ml of deionized water and sodium chloride is added to 0.2M concentration. The solution is brought to pH 7.5-8 with 2N sodium hydroxide and 300 ml of acetone are added. The pellet is separated by filtration. The solid obtained is solubilized with 100 ml deionized water and purified from the residual salts by diafiltration as described in step (i). The $^{13}$C-NMR analysis on a dried small amount of the oversulfated product is shown in FIG. 13.
(iv) The solution containing the product of step (iii) is passed onto a IR 120 H$^+$ cationic exchange resin (50 ml). After the passage of the solution the resin is washed with 3 volumes of deionized water. The pH of the flow through is more than 6. The acidic solution is brought to neutrality with pyridine. The solution is concentrated to 1/10 of the volume in a rotating evaporator at 40° C. under vacuum and freeze dried. The product obtained as pyridine salt is added with 500 ml of a solution of DMSO/methanol (9/1 V/V). The solution is kept at 60° C. for 2.5 hours and then added with 50 ml deionized water and finally treated with 1,650 ml acetone saturated with sodium chloride. The solid obtained is purified by diafiltration as described in step (i) and a solution at 10% concentration is obtained. The $^{13}$C-NMR analysis on a dried small amount in FIG. 14 shows a content of sulfate groups in position 6 of the amino sugar of 20%.
(v) The solution containing the product of step (iv) is passed onto a IR 120 H$^+$ cationic exchange resin (50 ml). After the passage of the solution the resin is washed with 3 volumes of deionized water. The pH of the flow through is more than 6. The acidic solution is brought to neutrality with an aqueous solution of 15% tetrabutylammoniun hydroxide. The solution is concentrated to ⅒ of the volume in a rotating evaporator under vacuum and freeze dried. The product as tetrabutylammonium salt is suspended in 200 ml DMF. The suspension is cooled to 0° C. and treated with 40 g of the adduct pyridine.$SO_3$ dissolved in 100 ml DMF. The sulfating agent is added one step. The solution is kept at 0° C. for 1.5 hours and then is treated with 750 ml acetone saturated with sodium chloride. The solid obtained is purified by diafiltration as described in step (i).

Figure 15:
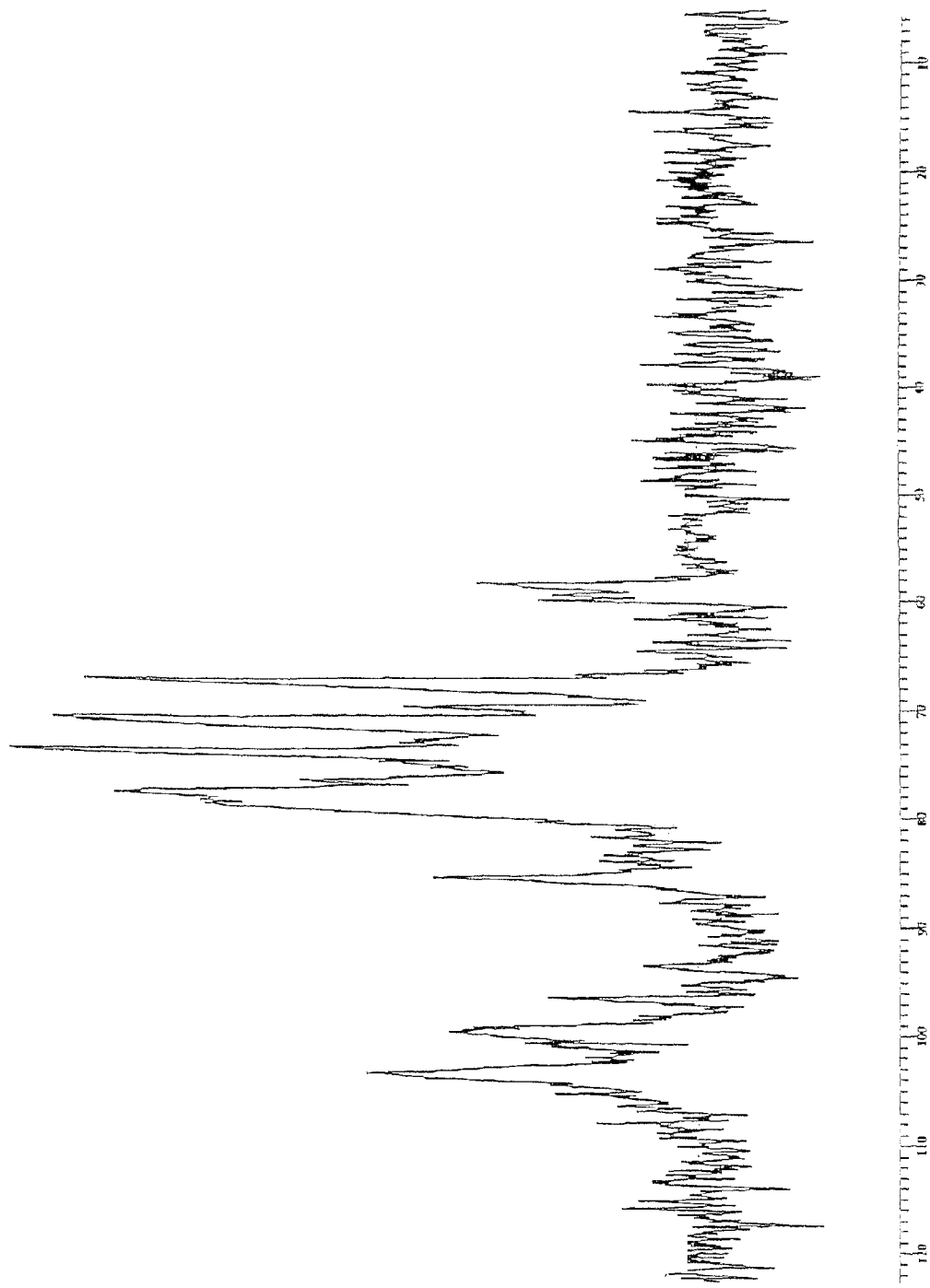
FIG. 15 shows the $^{13}$C-NMR spectrum of the compound obtained in Example 12 (vi).

(vi) The solution of step (v) is treated as described in step i) for N-sulfation, i.e. by adding an aqueous solution containing the solid obtained at the end of step (v), at 40° C., with sodium carbonate in one step and pyridine.$SO_3$ adduct in 10 minutes and isolating the N-deacetylated, N,O-sulfated, C5-epimerized.K5 polysaccharide thus obtained. The $^{13}$C-NMR on a dried small amount of the product obtained is shown in FIG. 15.

The compound obtained shows a mean molecular weight of 15,700 (see reference b in Tables 1 and 2), sulfate/carboxyl ratio of 2.55, iduronic acid content of 54%, N-sulfate content of >90%, 6-0 sulfate content of 85%, 3-O sulfate glucosamine content of 20%, iduronic acid 2-O-sulfate content of 25%, glucuronic acid 3-O-sulfate content of 30%, no O-disulfated uronic units, unsulfated uronic units content of about 40%. Taking into account the sulfate/carboxyl ratio of 2.55, by difference it is calculated that about 5% of sulfate groups are present in 2-O-sulfate glucuronic acid and 3-O-sulfate iduronic acid units. Furthermore, the compound obtained contains 55% of an ATIII high affinity fraction and the following in vitro anticoagulant activities compared to those of standard heparin taken as 100: anti-Xa 157, aPTT 78, anti-IIa 373, HCII 161. In respect of extractive heparin, the obtained 54% C5 epimerized, N,O-sulfate K5 polysaccharide shows an AntiXa/aPTT ratio of 2.01 and a HCII/Anti-Xa ratio of 1.02

Example 13

The C5-epimerized N,O-sulfate K5 obtained at the end of step (vi) of Example 12 is depolymerized with nitrous acid under controlled conditions as described in WO 82/03627. More particularly, 5 g of sample are dissolved in 250 ml of water and cooled to 4° C. with a thermostatic bath. The pH is brought to 2 with 1N hydrochloric acid, previously cooled to 4° C., then 10 ml of a solution of 1% sodium nitrite are added thereinto and, if necessary, the pH is brought to 2 with 1N hydrochloric acid. The mixture is kept under slow stirring for 15 minutes, the solution is neutralized with 1N NaOH, previously cooled to 4° C., then 250 mg of sodium borohydride dissolved in 13 ml of deionized water are added thereinto and the slow stirring is continued for 4 hours. The pH of the mixture is brought to 5 with 1N hydrochloric acid, then said mixture is let to stand under stirring for 10 minutes to destroy the excess of sodium borohydride, and finally neutralized with 1N NaOH. The product is recovered by precipitation with 3 volumes of ethanol and drying in a vacuum oven.

Figure 16:
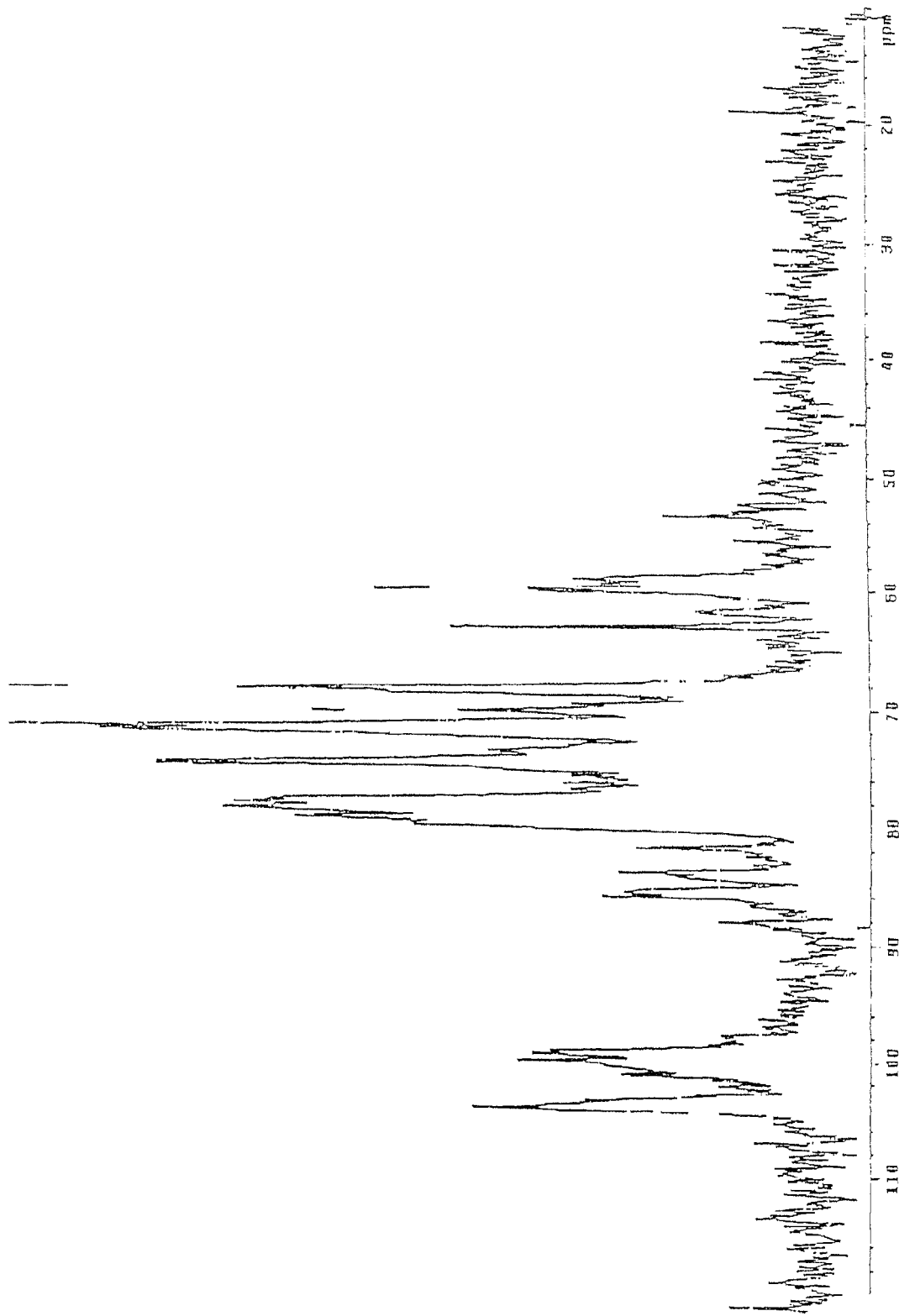
FIG. 16 shows the $^{13}$C-NMR spectrum of the low molecular weight compound obtained in Example 13.

In FIG. 16, the $^{13}$C-NMR spectrum of the compound thus obtained is shown. The compound has a mean molecular weight of 7,400, sulfate/carboxyl ratio of 2.55, iduronic acid content of 54%, N-sulfate content >90%, 6-O-sulfate content of 85%, 3-O-sulfate glucosamine content of 20%, iduronic acid 2-O-sulfate content of 25%, glucuronic acid 3-O-sulfate content of 30%, no O-disulfated uronic units, unsulfated uronic units content of 40%. Taking into account the sulfate/carboxyl ratio of 2.55, by difference it is calculated that 5% of sulfate groups are present in 2-O-sulfate glucuronic acid and 3-O-sulfate iduronic acid units. Furthermore, the glycosaminoglycan thus obtained contains 34% of ATIII high affinity fraction and the following in vitro anticoagulant activities compared to those of heparin taken as 100: anti-Xa 99, aPTT 52, anti-IIa 203, HCII 108. In comparison with said activities of the first International Standard of low molecular weight heparin (LMWH), taken as 100, the depolymerized, C5-epimerized N,O-sulfate K5 glycosaminoglycan thus obtained shows the following anticoagulant activities: anti Xa 117, aPTT 173, anti IIa 615 (HCII was not determined for LMWH). These results show that, for the C5-epimerized N,O-sulfate K5 thus obtained, anti-IIa/aPTT and anti-IIa/anti-Xa ratios are about four times and, respectively, twice as high as those of standard heparin; anti-IIa/aPTT and anti-IIa/anti-Xa ratios are about 3.5 times and, respectively, about five times as high as those of standard LMWH; and the HCII/aPTT ratio is about twice as high as that of standard heparin, anti-Xa and HCII activities being about as high as those of standard heparin and aPTT activity being about one half that of standard heparin. In particular, the obtained low molecular weight, 54% C5 epimerized, N,O-sulfate K5 polysaccharide shows an HCII/anti-Xa ratio as high as that of extractive heparin (1.09) and an AntiXa/aPTT ratio about twice in respect of that of extractive heparin (1.9).

Examples 14-16

By operating as described in Example 13, starting from the products of Examples 4, 5 and 7, glycosaminoglycans are obtained having respectively the characteristics shown in Table 3. Values represent a percentage against heparin (Fourth Int. Std) taken as 100. It results from this table that the glycosaminoglycan of Example 13 has a biochemical activity better than that of all the other low molecular weight glycosaminoglycans.

TABLE 3

|  | Anti Xa % | aPTT % | Anti IIa % | HCII % |
|---|---|---|---|---|
| Example 13 | 99 | 52 | 203 | 108 |
| Example 14 | 25 | 26 | 36 | 51 |
| Example 15 | 40 | 41 | 36 | 91 |
| Example 16 | 35 | 35 | 58 | 48 |

It is to be noted that Example 14, which was carried out starting from the product of Example 4 by operating under the same conditions as those of Example 11, was repeated several times. The activities of the products obtained were always very low and of the same order of magnitude as those given in Table 3 for Example 14.

Example 17

Example 12 is repeated using in step (ii) the recombinant enzyme obtained as described by Jin-Ping L. et al. ("Characterization of D-glucuronosyl-C5 epimerase involved in the biosynthesis of heparin and heparan sulfate" Journal Biological Chemistry, 2001, 276, 20069-20077). The compound obtained shows a mean molecular weight of 14,900 (see reference b in Tables 1 and 2), sulfate/carboxyl ratio of 2.7, iduronic acid content of 54%, N-sulfate content of >90%, 6-0 sulfate content of 90%, 3-O sulfate glucosamine content of 20%, iduronic acid 2-O-sulfate content of 30%, glucuronic acid 3-O-sulfate content of 35%, no O-disulfated uronic units, unsulfated uronic units content of about 30%. Taking into account the sulfate/carboxyl ratio of 2.7, by difference it is calculated that about 5% of sulfate groups are present in glucuronic acid 2-O-sulfate and iduronic acid 3-O-sulfate units. Furthermore, the compound obtained shows the following in vitro anticoagulant activities compared to those of standard heparin taken as 100: anti-Xa 166, aPTT 76, anti-IIa 400, HCII 283. Thus, in respect of extractive heparin, the obtained 54% C5 epimerized, N,O-sulfate K5 polysaccharide shows an AntiXa/aPTT ratio of 1.31 and a HCII/Anti-Xa ratio of 2.41.

Without further elaboration, it is believed that one skilled in the art can, using the preceding description, utilize the present invention to its fullest extent. The preceding preferred specific embodiments are, therefore, to be constructed as merely illustrative, and not limitative of the remainder of the disclosure in any way whatsoever.

The entire disclosure of all application, patents and publications, cited above, and a corresponding Italian application filed March 2000, the assignee of record being INALCO, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A glycosaminoglycan derived from K5 polysaccharide, epimerized at least till 40% of iduronic acid with respect to the total uronic acids, having molecular weight from 2,000 to 30,000 D, containing from 25 to 50% on weight of the chains with high affinity for ATIII and having an anticoagulant and antithrombotic activity expressed as ratio HCII/Anti-Xa comprised between 1.5 and 4, as produced by a process comprising in sequence: (a) preparation of K5 polysaccharide from *Escherichia coli*, (b) N-deacetylation and N-sulfation of the K5 polysaccharide, (c) 40%-60% C5 epimerization of D-glucuronic acid to L-iduronic acid, (d) oversulfation, (e) selective O-desulfation, (f) selective 6-O sulfation, and (g) N-sulfation.

2. A glycosaminoglycan according to claim 1, wherein the molecular weight is between 4,000 and 8,000 D.

3. A glycosaminoglycan according to claim 1, wherein the molecular weight is between 18,000 and 30,000 D.

4. A process for the preparation of a glycosaminoglycan derived from K5 polysaccharide as defined in claim 1, comprising in sequence: (a) preparation of K5 polysaccharide from *Escherichia coli*, (b) N-deacetylation and N-sulfation, (c) 40%-60% C5 epimerization of D-glucuronic acid to L-iduronic acid, (d) oversulfation, (e) selective O-desulfation, (f) selective 6-O sulfation and (g) N-sulfation; wherein said C5 epimerization is performed by glucuronosyl C5 epimerase in solution or in immobilized form in presence of divalent cations.

5. A process according to claim 4, wherein said epimerase is selected from the group consisting of recombinant glucuronosyl C5 epimerase, glucuronosyl C5 epimerase from murine mastocytoma and glucuronosyl C5 epimerase extracted from bovine liver.

6. A process according to claim 4, wherein said divalent cations comprise at least one selected from the group consisting of Ba, Ca, Mg and Mn ions.

7. A process according to claim 4, wherein said C5 epimerization is performed in solution by dissolving an amount of epimerase comprised between $1.2 \times 10^7$ and $1.2 \times 10^{11}$ cpm in 2-2,000 ml of 25 mM Hepes buffer at a pH between 5.5 and 7.4 containing from 0.001 to 10 g of N-deacetylated N-sulfated K5 and one or a combination of said cations at a concentration comprised between 10 and 60 mM.

8. A process according to claim 7, wherein said C5 epimerization in solution is performed at a temperature between 30 and 40° C. for a time comprised between 1 and 24 hours.

9. A process according to claim 4, wherein said C5 epimerization is performed by epimerase in its immobilized form and comprises recirculating 20-1,000 ml of a solution of 25 mM Hepes at pH from 6 to 7.4 containing 0.001-10 g of N-deacetylated N-sulfated K5 and one of said cations at a concentration between 10 and 60 mM through a column containing from $1.2 \times 10^7$ to $3 \times 10^{11}$ cpm of the immobilized epimerase on an inert support.

10. A process according to claim 9, wherein said C5 epimerization is performed at a temperature between 30 and 40° C. recirculating said solution with a flow rate of 30-160 ml/hour for a time between 1 and 24 hours.

11. A process according to claim 4, wherein said selective O-desulfation is carried out by reacting a tertiary or quaternary ammonium salt of the oversulfated product with a solution dimethyl sulfoxide/methanol 9/1 (V/V) at 60° C. for 2-4 hours.

12. A process according to claim 4, wherein said C5 epimerization is performed by glucuronosyl C5 epimerase in solution or in immobilized form in presence of divalent cations, said selective O-desulfation is carried out by reacting a tertiary or quaternary ammonium salt of the oversulfated product with a solution dimethyl sulfoxide/methanol 9/1 (V/V) at 60° C. for 3 hours and said selective O-sulfation is performed by reacting a tertiary or quaternary ammonium salt of the selectively O-desulfated product with a calculated amount of a sulfating agent at a temperature of 0-5° C. for 0.5-3 hours.

13. A process according to claim 12, wherein said selective O-sulfation is carried out for 1.5 hours using a pyridine.sulfur trioxide adduct as sulfating agent.

14. A process for the preparation of K5 glycosaminoglycans comprising the steps of (i) N-deacetylation and N-sulfation of the polysaccharide K5, (ii) 40%-60% C5-epimerization of the carboxyl group of the glucuronic acid moiety to the corresponding iduronic acid moiety, (iii) oversulfation, (iv) selective O-desulfation, (v) 6-O-sulfation, and (vi) N-sulfation; wherein step (iv) comprises treating the oversulfated product obtained at the end of step (iii) with a mixture methanol/dimethyl sulfoxide for a period of time of from 135 to 165 minutes.

15. A process according to claim 14 in which said period of time is of about 150 minutes.

16. A process according to claim 14 in which said treatment of the oversulfated product obtained at the end of step (iii) with a mixture methanol/dimethyl sulfoxide is made for a period of time of about 150 minutes at a temperature of about 60° C.

17. A process for the preparation of glycosaminoglycans, which comprises (i) reacting polysaccharide K5 with a N-deacetylating agent, then treating the N-deacetylated product with a N-sulfating agent;

(ii) submitting the N-sulfate K5 thus obtained to a C5-epimerization by glucuronosyl C5 epimerase to obtain a C5-epimerized N-sulfate K5 in which the iduronic/glucuronic ratio is from 60/40 to 40/60;

(iii) converting the C5 epimerized N-sulfate K5, having a content of 40 to 60% iduronic acid over the total uronic acids, into a tertiary or quaternary salt thereof, then treating the salt thus obtained with an O-sulfating agent in an aprotic polar solvent at a temperature of 40-60° C. for 10-20 hours;

(iv) treating an organic base salt of the O-oversulfated product thus obtained with a mixture of dimethyl sulfoxide/methanol at 50-70° C. for 135-165 minutes;

(v) treating an organic base salt of the partially O-desulfated product thus obtained with an O-sulfating agent at a temperature of 0-5° C.; and (vi) treating the product thus obtained with a N-sulfating agent;

whatever product obtained at the end of one of steps (ii) to (vi) being optionally submitted to a depolymerization.

18. A process according to claim 17, wherein a previously purified K5 polysaccharide is used as starting material.

19. A process according to claim 17, wherein in step (i) hydrazine or a salt thereof or an alkaline metal hydroxide is used as a N-deacetylating agent and pyridine.sulfur trioxide or trimethylamine.sulfur trioxide adduct is used as a N-sulfating agent.

20. A process according to claim 17, wherein in step (ii) said C5 epimerization is performed by glucuronosyl C5 epimerase in solution or in immobilized form in presence of divalent cations and comprises recirculating 20-1,000 ml of a solution of Hepes at a pH 7 of from 6 to 7.4 containing 0.001-10 g to N-deacetylated N-sulfated K5 polysaccharide and one of said cations at a concentration between 1 mM and 60 Mm through a column containing from $1.2 \times 10^7$ to $3 \times 10^{11}$ cpm of the immobilized epimerase on an inert support.

21. A process according to claim 20, wherein said divalent cations comprise at least one from the group consisting of Ba, Ca, Mg and Mn ions.

22. A process according to claim 17, wherein in step (ii) said epimerase is selected from the group consisting of recombinant glucuronosyl C5 epimerase, glucuronosyl C5 epimerase from murine mastocytoma and glucuronosyl C5 epimerase extracted from bovine liver.

23. A process according to claim 17, wherein in step (iv) the reaction is carried out in dimethyl sulfoxide/methanol 9/1 (V/V) at about 60° C. for about 150 minutes.

24. A process according to claim 17, wherein the product obtained at the end of step (vi) is submitted to a nitrous acid depolymerization followed by a reduction by sodium borohydride.

25. A process according to claim 17, wherein a previously purified K5 is used as starting material and in step (iv) the reaction is carried out in dimethyl sulfoxide/methanol 9/1 (V/V) at about 60° C. for about 150 minutes, and the C5-epimerized N,O-sulfate K5 glycosaminoglycan obtained at the end of step (vi) is submitted to a nitrous acid depolymerization followed by a reduction by sodium borohydride.

26. A process according to claim 17, wherein the glycosaminoglycan thus obtained is isolated in form of its sodium salt.

27. A process according to claim 26, wherein said sodium salt is further converted to another salt of said glycosaminoglycan.

28. A process according to claim 27, wherein said other salt is another alkaline metal, or an alkali earth metal, ammonium, tri($C_1$-$C_4$)alkylammonium, tetra($C_1$-$C_4$)alkylammonium aluminium or zinc salt.

29. A glycosaminoglycan constituted by a mixture of chains in which at least 90% of said chains has the formula I

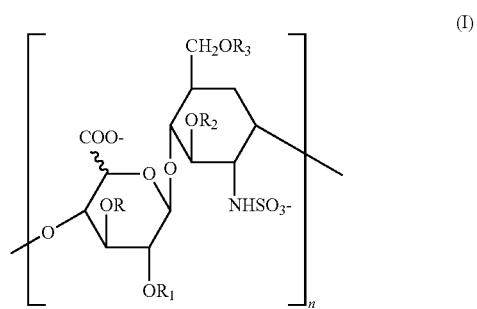

wherein 40-60% of the uronic acid units are those of iduronic acid, n is an integer from 3 to 100, R, $R_1$, $R_2$ and $R_3$ represent a hydrogen atom or a $SO_3^-$ group and from about 65% to about 50% of R, $R_1$, $R_2$ and $R_3$ being hydrogen and the remaining being $SO_3^-$ groups distributed as follows
(i) $R_3$ is from about 85% to about 95% $SO_3^-$;
(ii) $R_2$ is from about 17 to about 21% $SO_3^-$;
(iii) $R_1$ is from about 15 to about 35% $SO_3^-$ in iduronic units and 0 to 5% $SO_3^-$ in glucuronic units;
(iv) R is from about 20 to about 40% $SO_3^-$ in glucuronic units and 0 to 5% in iduronic units;
(v) the sum of the $SO_3^-$ percent in $R_1$, glucuronic units, and in R, iduronic units, is from 3 to 7%;
$R_1$ and R being not simultaneously $SO_3^-$ and being both hydrogen in 25-45% of the uronic acid units; the sulfation degree being from about 2.3 to about 2.9, and the corresponding cation being a chemically or pharmaceutically acceptable one.

30. A glycosaminoglycan of claim 29, wherein said corresponding cation is an alkaline metal, alkali earth metal, aluminum or zinc ion.

31. A glycosaminoglycan of claim 29, wherein said corresponding cation is sodium or calcium ion.

32. A pharmaceutical composition comprising a pharmacologically effective amount of a glycosaminoglycan constituted by a mixture of chains in which at least 90% of said chains has the formula I

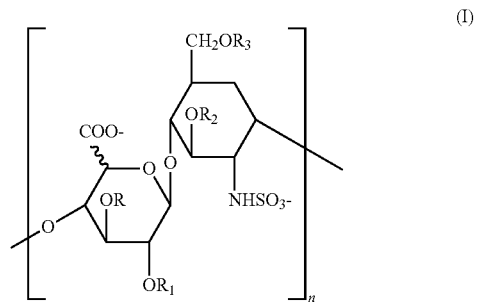

wherein 40-60% of the uronic acid units are those of iduronic acid, n is an integer from 3 to 100, R, $R_1$, $R_2$ and $R_3$ represent a hydrogen atom or a $SO_3^-$ group and from about 65% to about 50% of R, $R_1$, $R_2$ and $R_3$ being hydrogen and the remaining being $SO_3^-$ groups distributed as follows
(i) $R_3$ is from about 85% to about 95% $SO_3^-$;
(ii) $R_2$ is from about 17 to about 21% $SO_3^-$;
(iii) $R_1$ is from about 15 to about 35% $SO_3^-$ in iduronic units and 0 to 5% $SO_3^-$ in glucuronic units;

(iv) R is from about 20 to about 40% $SO_3^-$ in glucuronic units and 0 to 5% in iduronic units;

(v) the sum of the $SO_3^-$ percent in $R_1$, glucuronic units, and in R, iduronic units, is from 3 to 7%;

$R_1$ and R being not simultaneously $SO_3^-$ and being both hydrogen in 25-45% of the uronic acid units; the sulfation degree being from about 2.3 to about 2.9, and the corresponding cation being a pharmaceutically acceptable one, as an active ingredient, and a pharmaceutically acceptable carrier.

33. A composition of claim 32, wherein said glycosaminoglycan is constituted by a mixture of chains in which at least 80% of said chains have the formula I, in which n is from 3 to 15.

34. A composition of claim 33, wherein said mixture of chains has a molecular weight distribution ranging from about 2,000 to about 10,000 with a mean molecular weight of from about 4,000 to about 8,000.

35. A method for treating thrombosis in a mammal which comprises administering to said mammal an effective amount of the glycosaminoglycan of claim 29.

36. A method according to claim 35, wherein said effective amount is administered in a pharmaceutical composition containing from 5 to 100 mg of said glycosaminoglycan.

37. A method for treating thrombosis in a mammal which comprises administering to said mammal an effective amount of the glycosaminoglycan of claim 1.

38. A method according to claim 37, wherein said effective amount is administered in a pharmaceutical composition containing from 5 to 100 mg of said glycosaminoglycan.

* * * * *